United States Patent
Ramaswamy

(10) Patent No.: US 10,443,046 B2
(45) Date of Patent: Oct. 15, 2019

(54) ARRAYS OF MEMORY CELLS INDIVIDUALLY COMPRISING A CAPACITOR AND AN ELEVATIONALLY-EXTENDING TRANSISTOR, METHODS OF FORMING A TIER OF AN ARRAY OF MEMORY CELLS, AND METHODS OF FORMING AN ARRAY OF MEMORY CELLS INDIVIDUALLY COMPRISING A CAPACITOR AND AN ELEVATIONALLY-EXTENDING TRANSISTOR

(71) Applicant: Micron Technology, Inc., Boise, ID (US)

(72) Inventor: Durai Vishak Nirmal Ramaswamy, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 16/238,689

(22) Filed: Jan. 3, 2019

(65) Prior Publication Data
US 2019/0136207 A1 May 9, 2019

Related U.S. Application Data

(63) Continuation of application No. 15/818,934, filed on Nov. 21, 2017, now Pat. No. 10,202,583, which is a
(Continued)

(51) Int. Cl.
*H01L 27/00* (2006.01)
*C12N 7/00* (2006.01)
(Continued)

(52) U.S. Cl.
CPC ............ *C12N 7/00* (2013.01); *C12N 15/1133* (2013.01); *C12Q 1/701* (2013.01); *C12Q 1/705* (2013.01); *H01L 27/10808* (2013.01); *H01L 27/10814* (2013.01); *H01L 27/10852* (2013.01); *H01L 27/10873* (2013.01); *H01L 27/11507* (2013.01); *H01L 28/91* (2013.01);
(Continued)

(58) Field of Classification Search
CPC . H01L 27/108–10841; H01L 27/10897; H01L 27/1116; H01L 27/11286
See application file for complete search history.

(56) References Cited

U.S. PATENT DOCUMENTS 8,847,353 B2 * 9/2014 Hasunuma .......... H01L 27/0207
257/307
9,287,270 B2 3/2016 Oh et al.
(Continued)

FOREIGN PATENT DOCUMENTS

| CN | 1500292 | 5/2004 |
|---|---|---|
| KR | 2010-0062609 | 6/2010 |
| TW | 201225260 | 6/2012 |

*Primary Examiner* — Nicholas J Tobergte
(74) *Attorney, Agent, or Firm* — Well St. John P.S.

(57) ABSTRACT

A method of forming a tier of an array of memory cells within an array area, the memory cells individually comprising a capacitor and an elevationally-extending transistor, the method comprising using two, and only two, sacrificial masking steps within the array area of the tier in forming the memory cells. Other methods are disclosed, as are structures independent of method of fabrication.

23 Claims, 36 Drawing Sheets

Related U.S. Application Data continuation of application No. 15/402,463, filed on Jan. 10, 2017, now Pat. No. 9,837,420.

(51) Int. Cl.

| | | |
|---|---|---|
| *H01L 27/108* | (2006.01) | |
| *H01L 49/02* | (2006.01) | |
| *H01L 27/11507* | (2017.01) | |
| *C12N 15/113* | (2010.01) | |
| *C12Q 1/70* | (2006.01) | |
| *H01L 29/66* | (2006.01) | |
| *H01L 29/78* | (2006.01) | |

(52) U.S. Cl.
CPC .... *H01L 29/66666* (2013.01); *H01L 29/7827* (2013.01); *C12N 2310/113* (2013.01); *C12N 2310/14* (2013.01); *C12N 2310/141* (2013.01); *C12N 2310/3231* (2013.01); *C12N 2710/16211* (2013.01); *C12N 2710/16263* (2013.01); *C12Q 2600/136* (2013.01); *C12Q 2600/158* (2013.01); *H01L 27/10838* (2013.01)

(56) References Cited

U.S. PATENT DOCUMENTS

| | | | |
|---|---|---|---|
| 9,337,149 B2* | 5/2016 | Im | H01L 27/10855 |
| 9,799,724 B2* | 10/2017 | Lee | H01L 27/0805 |
| 10,014,305 B2* | 7/2018 | Ramaswamy | H01L 28/90 |
| 2002/0109176 A1 | 8/2002 | Forbes et al. | |
| 2005/0164454 A1 | 7/2005 | Leslie | |
| 2010/0135064 A1 | 6/2010 | Kim et al. | |
| 2012/0153371 A1 | 6/2012 | Chen et al. | |
| 2018/0096947 A1* | 4/2018 | Lee | H01L 23/544 |
| 2018/0315658 A1* | 11/2018 | Ramaswamy | H01L 28/90 |

\* cited by examiner

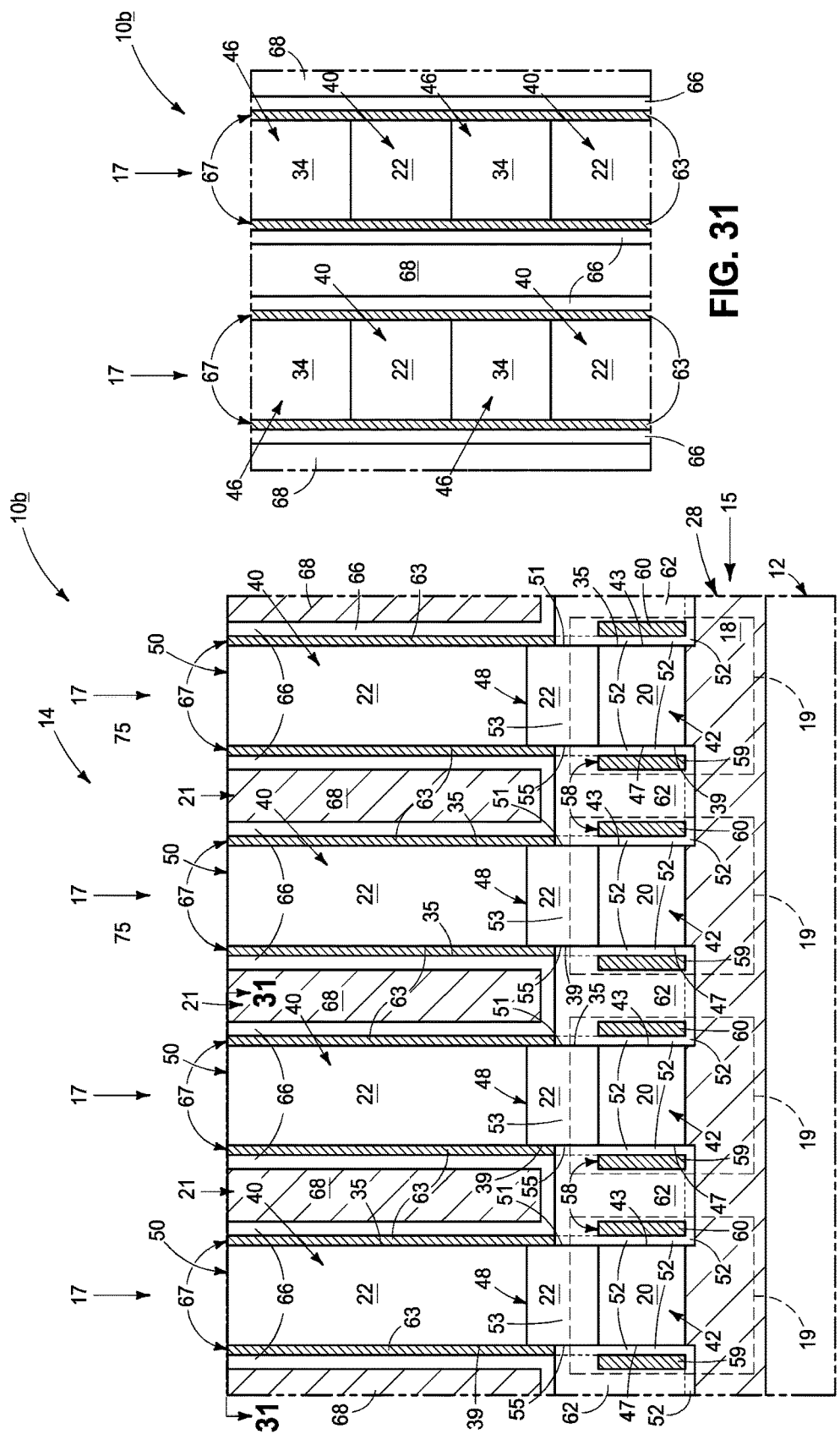

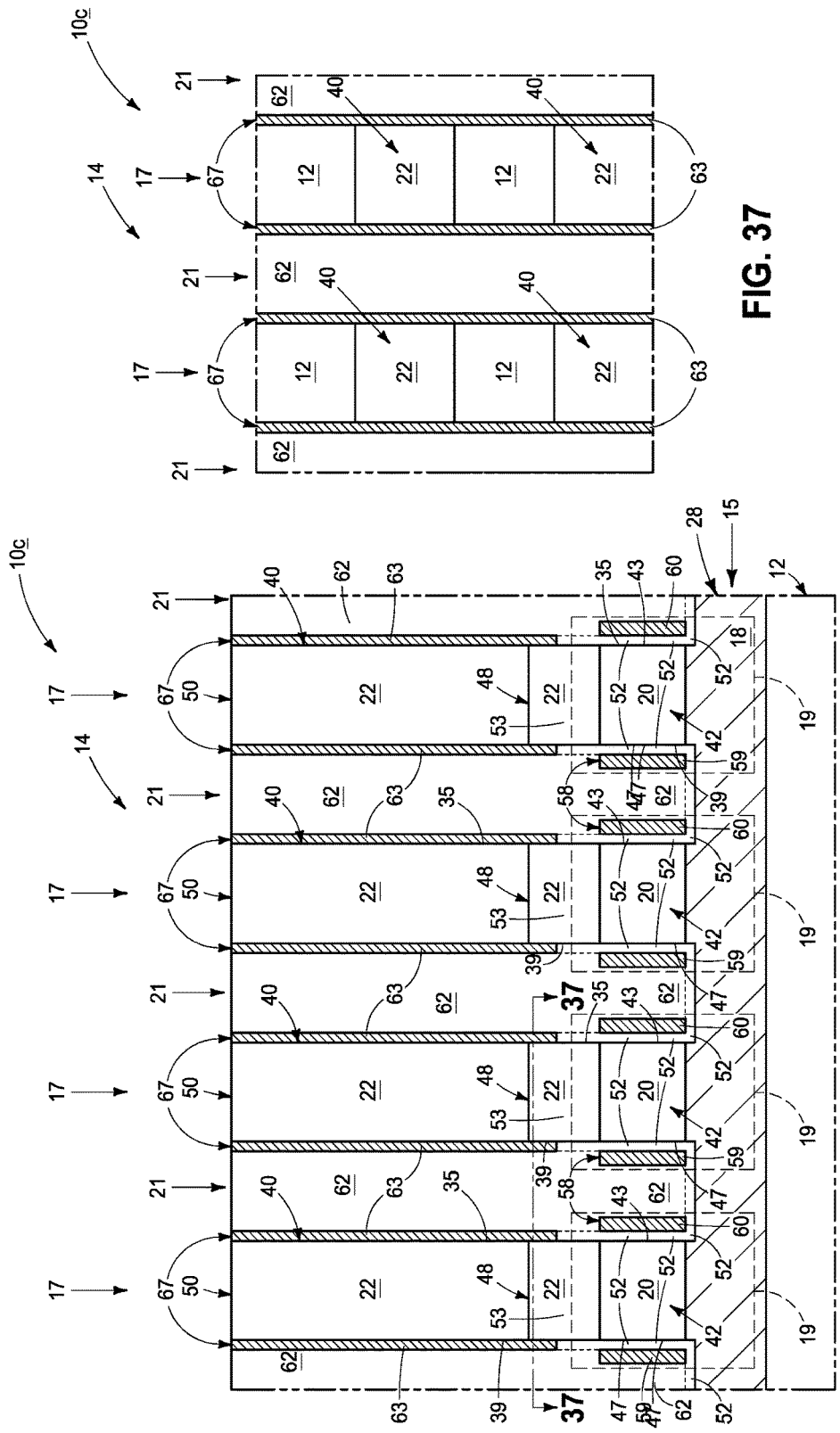

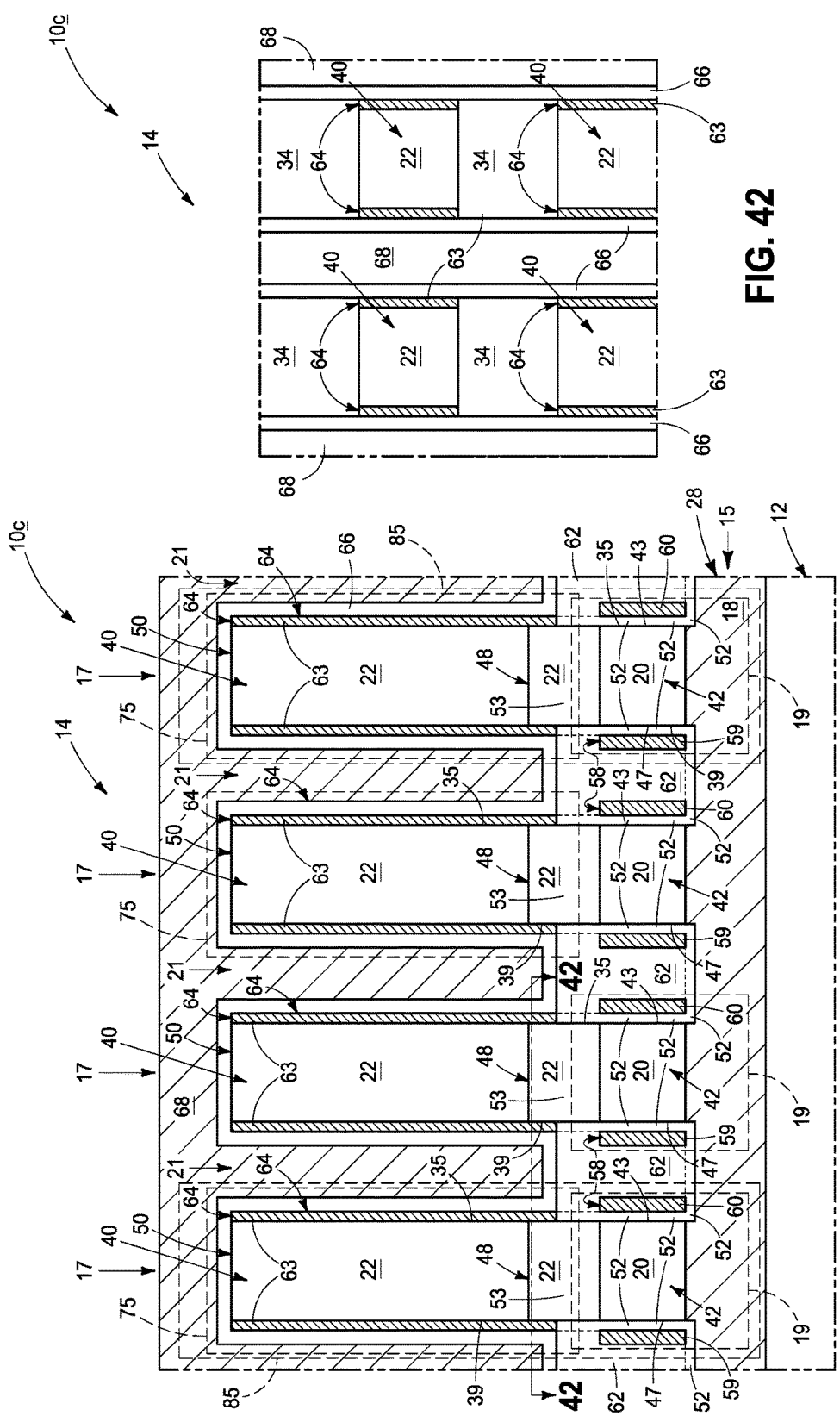

ARRAYS OF MEMORY CELLS INDIVIDUALLY COMPRISING A CAPACITOR AND AN ELEVATIONALLY-EXTENDING TRANSISTOR, METHODS OF FORMING A TIER OF AN ARRAY OF MEMORY CELLS, AND METHODS OF FORMING AN ARRAY OF MEMORY CELLS INDIVIDUALLY COMPRISING A CAPACITOR AND AN ELEVATIONALLY-EXTENDING TRANSISTOR

RELATED PATENT DATA

This patent resulted from a continuation application of U.S. patent application Ser. No. 15/818,934, filed Nov. 21, 2017, entitled "Arrays Of Memory Cells Individually Comprising A Capacitor And An Elevationally-Extending Transistor, Methods Of Forming A Tier Of An Array Of Memory Cells, And Methods Of Forming An Array Of Memory Cells Individually Comprising A Capacitor And An Elevationally-Extending Transistor", naming Durai Vishak Nirmal Ramaswamy as inventor, which was a continuation application of U.S. patent application Ser. No. 15/402,463, filed Jan. 10, 2017, entitled "Arrays Of Memory Cells Individually Comprising A Capacitor And An Elevationally-Extending Transistor, Methods Of Forming A Tier Of An Array Of Memory Cells, And Methods Of Forming An Array Of Memory Cells Individually Comprising A Capacitor And An Elevationally-Extending Transistor", naming Durai Vishak Nirmal Ramaswamy as inventor, now U.S. Pat. No. 9,837,420, the disclosures of which are incorporated by reference.

TECHNICAL FIELD

Embodiments disclosed herein pertain to methods of forming a tier of an array of memory cells, to methods of forming an array of memory cells individually comprising a capacitor and an elevationally-extending transistor, and to arrays of memory cells individually comprising a capacitor and an elevationally-extending transistor.

BACKGROUND

Memory is one type of integrated circuitry, and is used in computer systems for storing data. Memory may be fabricated in one or more arrays of individual memory cells. Memory cells may be written to, or read from, using digit lines (which may also be referred to as bit lines, data lines, sense lines, or data/sense lines) and access lines (which may also be referred to as word lines). The digit lines may conductively interconnect memory cells along columns of the array, and the access lines may conductively interconnect memory cells along rows of the array. Each memory cell may be uniquely addressed through the combination of a digit line and an access line.

Memory cells may be volatile or non-volatile. Non-volatile memory cells can store data for extended periods of time including when the computer is turned off. Volatile memory dissipates and therefore requires being refreshed/rewritten, in many instances multiple times per second. Regardless, memory cells are configured to retain or store memory in at least two different selectable states. In a binary system, the states are considered as either a "0" or a "1". In other systems, at least some individual memory cells may be configured to store more than two levels or states of information.

A capacitor is one type of electronic component that may be used in a memory cell. A capacitor has two electrical conductors separated by electrically insulating material. Energy as an electric field may be electrostatically stored within such material. Depending on composition of the insulator material, that stored field will be volatile or non-volatile. For example, a capacitor insulator material including only $SiO_2$ will be volatile. One type of non-volatile capacitor is a ferroelectric capacitor which has ferroelectric material as at least part of the insulating material. Ferroelectric materials are characterized by having two stable polarized states and thereby can comprise programmable material of a capacitor and/or memory cell. The polarization state of the ferroelectric material can be changed by application of suitable programming voltages, and remains after removal of the programming voltage (at least for a time). Each polarization state has a different charge-stored capacitance from the other, and which ideally can be used to write (i.e., store) and read a memory state without reversing the polarization state until such is desired to be reversed. Less desirable, in some memory having ferroelectric capacitors the act of reading the memory state can reverse the polarization. Accordingly, upon determining the polarization state, a re-write of the memory cell is conducted to put the memory cell into the pre-read state immediately after its determination. Regardless, a memory cell incorporating a ferroelectric capacitor ideally is non-volatile due to the bi-stable characteristics of the ferroelectric material that forms a part of the capacitor. Other programmable materials may be used as a capacitor insulator to render capacitors non-volatile.

BRIEF DESCRIPTION OF THE DRAWINGS

FIG. 30 is a view of the FIG. 28 construction at a processing step subsequent to that shown by FIG. 28.

FIG. 31 is a top view through line 31-31 in FIG. 30.

FIG. 36 is a diagrammatic front elevational view of a substrate construction in process in accordance with an embodiment of the invention.

FIG. 37 is a cross-sectional view taken through line 37-37 in FIG. 36.

FIG. 41 is a view of the FIG. 40 construction at a processing step subsequent to that shown by FIG. 40.

FIG. 42 is a cross-sectional view taken through line 42-42 in FIG. 41.

DETAILED DESCRIPTION OF EXAMPLE EMBODIMENTS

Embodiments of the invention encompass methods of forming an array of memory cells individually comprising a capacitor and an elevationally-extending transistor and arrays of such memory cells independent of method of manufacture. Example embodiments of methods of forming such arrays are initially described with reference to FIGS. 1-22.

Figure 1:
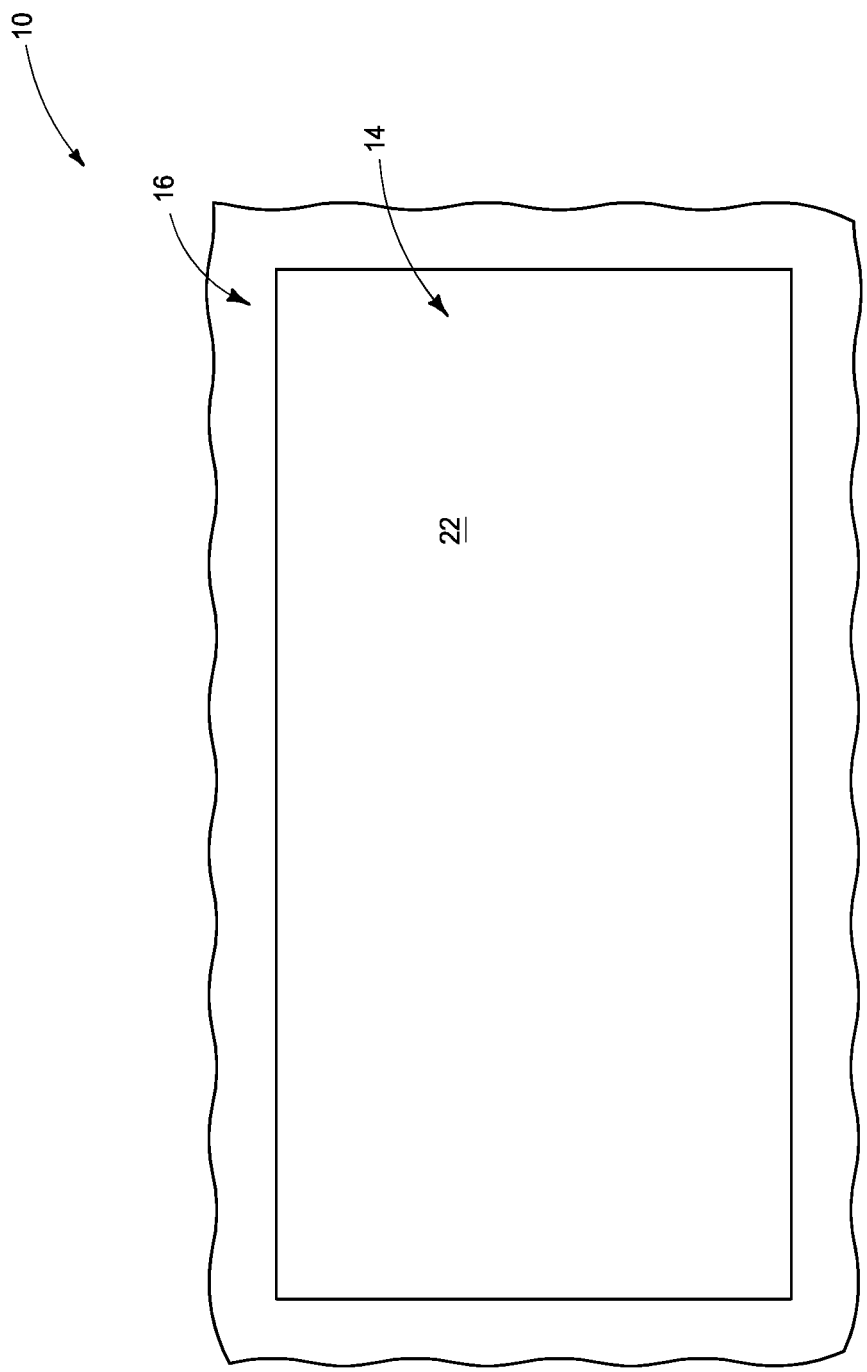
FIG. 1 is a diagrammatic top-plan view of a substrate construction in process in accordance with an embodiment of the invention.
Figure 2:
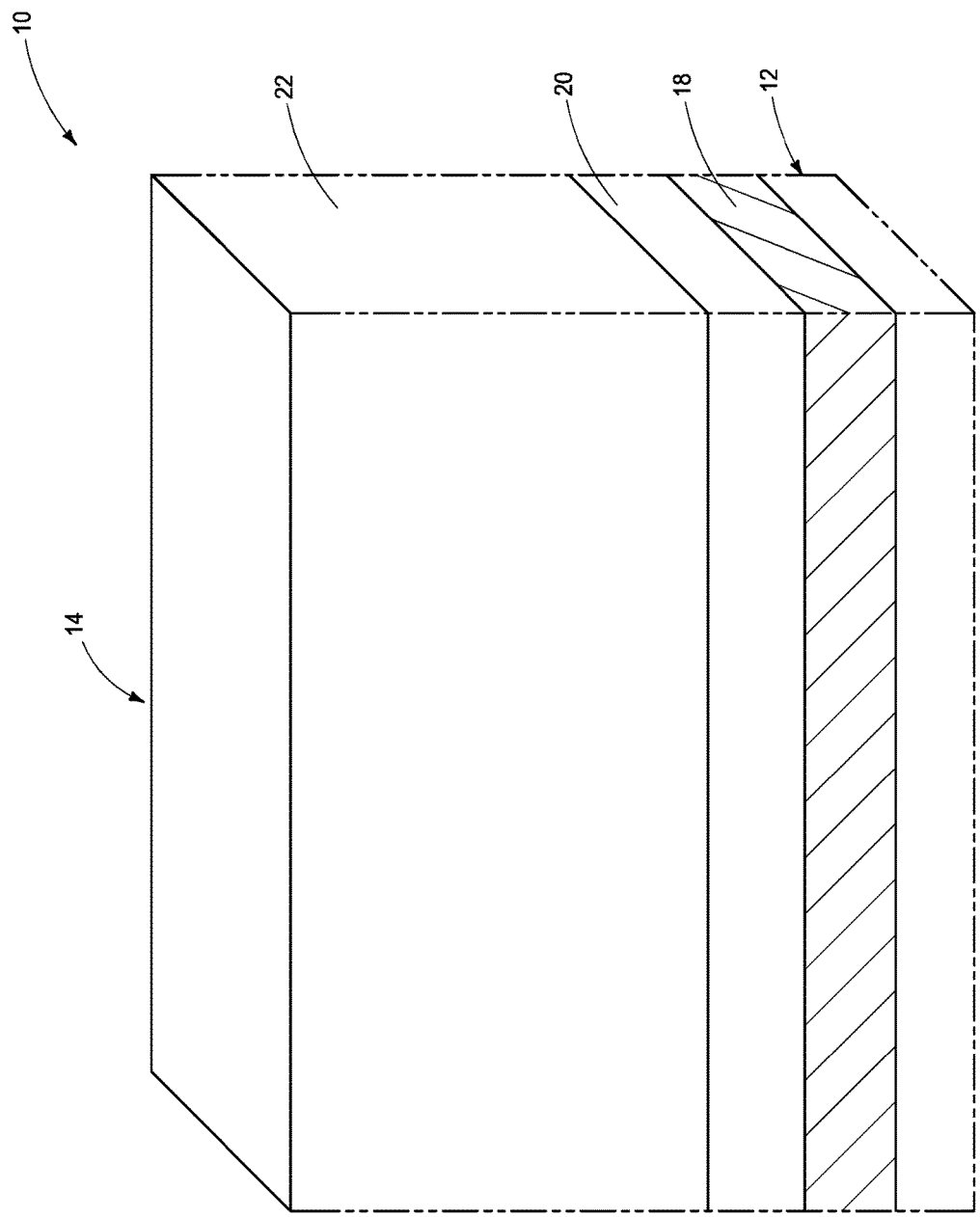
FIG. 2 is a perspective view of a portion of FIG. 1.

Referring to FIGS. 1 and 2, such depict a portion of a substrate fragment or construction 10 comprising a base substrate 12 having an array or array area 14 within which an array of memory cells individually comprising an elevationally-extending transistor and a capacitor will be fabricated. An area 16 (FIG. 1) is peripheral to array 14 and may be fabricated to include circuit components (i.e., circuitry). Individual memory cells will be fabricated within array 14 and array 14 may comprise rows of access lines and columns of digit lines. Use of "rows" and "columns" herein is with respect to a series of access lines and a series of digit lines, respectively, and longitudinally along which individual memory cells have been or will be formed within array 14. The rows may be straight and/or curved and/or parallel and/or non-parallel relative one another, as may be the columns. Further, the rows and columns may intersect relative one another at 90° or at one or more other angles. Peripheral area 16 may be considered as starting and array 14 may be considered as stopping where a repeating pattern of memory cells stops (e.g., at peripheral edges of such a repeating pattern) although the rows of access lines and/or the columns of digit lines may and likely will extend into peripheral area 16.

Base substrate 12 may include any one or more of conductive/conductor/conducting (i.e., electrically herein), semiconductive, or insulative/insulator/insulating (i.e., electrically herein) materials. In the context of this document, a conductive/conductor/conducting material has compositional intrinsic electrical conductivity of at least $3 \times 10^4$ Siemens/cm (i.e., at 20° C. everywhere herein) as opposed to electrical conductivity that could occur by movement of positive or negative charges through a thin material that is otherwise intrinsically insulative. A non-conductive/non-conductor/non-conducting material has compositional intrinsic electrical conductivity of less than $3 \times 10^4$ Siemens/cm. An insulative/insulator/insulating material has compositional intrinsic electrical conductivity of less than $1 \times 10^{-9}$ Siemen/cm (i.e., it is electrically resistive as opposed to being conductive or semiconductive). A semiconductive material has compositional intrinsic electrical conductivity of less than $3 \times 10^4$ Siemens/cm to $1 \times 10^{-9}$ Siemen/cm. Various materials are shown above base substrate 12. Materials may be aside, elevationally inward, or elevationally outward of the depicted FIGS. 1 and 2 materials. For example, other partially or wholly fabricated components of integrated circuitry may be provided somewhere above, about, or within substrate 12. Control and/or other peripheral circuitry for operating components within a memory array may also be fabricated, and may or may not be wholly or partially within an array or sub-array. Further, multiple sub-arrays may also be fabricated and operated independently, in tandem, or otherwise relative one another. As used in this document, a "sub-array" may also be considered as an array. Regardless, any of the materials, regions, and structures described herein may be homogenous or non-homogenous, and regardless may be continuous or discontinuous over any material which such overlie. Further, unless otherwise stated, each material may be formed using any suitable existing or yet-to-be-developed technique, with atomic layer deposition, chemical vapor deposition, physical vapor deposition, epitaxial growth, diffusion doping, and ion implanting being examples.

Digit line material 18 (FIG. 2) has been formed over substrate 12, channel-comprising material 20 has been formed above digit line material 18, and source/drain-comprising material 22 has been formed above channel-comprising material 20. In this document, unless otherwise indicated, "elevational(ly)", "higher", "upper", "lower", "top", "atop", "bottom", "above", "below", "under", "beneath", "up", and "down" are generally with reference to the vertical direction. Further, "vertical" and "horizontal" as used herein are directions that are perpendicular or within 10 degrees of perpendicular relative one another independent of orientation of the substrate in three-dimensional space. "Horizontal" refers to a general direction (i.e., within 10 degrees) along a primary substrate surface and may be relative to which the substrate is processed during fabrication. Also, "extend(ing) elevationally" and "elevationally-extending" in this document encompasses a range from vertical to no more than 45° from vertical. Further, "extend (ing) elevationally", "elevationally-extending", and "vertical(ly)" with respect to a field effect transistor are with reference to orientation of the transistor's channel length along which current flows in operation between two source/drain regions of the transistor that are at two different elevations. Example conductive digit line material 18 is one or more of elemental metal, a mixture or alloy of two or more elemental metals, conductive metal compounds, and conductively-doped semiconductive materials, with TiN being one specific example. Example channel-comprising material 20 is semiconductive material suitably doped with conductivity enhancing material, with suitably doped polysilicon being one specific example. Example source/drain-comprising material 22 is one or more of elemental metal, a mixture or alloy of two or more elemental metals, conductive metal compounds, and conductively-doped semiconductive materials, with conductively doped polysilicon being one specific example. Example thicknesses for materials 18, 20, and 22 are 150 to 350 Angstroms, 400 to 900 Angstroms, and 2,000 to 4,000 Angstroms, respectively.

In this document, "thickness" by itself (no preceding directional adjective) is defined as the mean straight-line distance through a given material or region perpendicularly from a closest surface of an immediately adjacent material of different composition or of an immediately adjacent region. Additionally, the various materials or regions described herein may be of substantially constant thickness or of variable thicknesses. If of variable thickness, thickness refers to average thickness unless otherwise indicated, and such material or region will have some minimum thickness and some maximum thickness due to the thickness being variable. As used herein, "different composition" only requires those portions of two stated materials or regions that may be directly against one another to be chemically and/or physically different, for example if such materials or regions are not homogenous. If the two stated materials or regions are not directly against one another, "different composition" only requires that those portions of the two stated materials or regions that are closest to one another be chemically and/or physically different if such materials or regions are not homogenous. In this document, a material, region, or structure is "directly against" another when there is at least some physical touching contact of the stated materials, regions, or structures relative one another. In contrast, "over", "on", "adjacent", "along", and "against" not preceded by "directly" encompass "directly against" as well as construction where intervening material(s), region(s), or structure(s) result(s) in no physical touching contact of the stated materials, regions, or structures relative one another.

Figure 3:
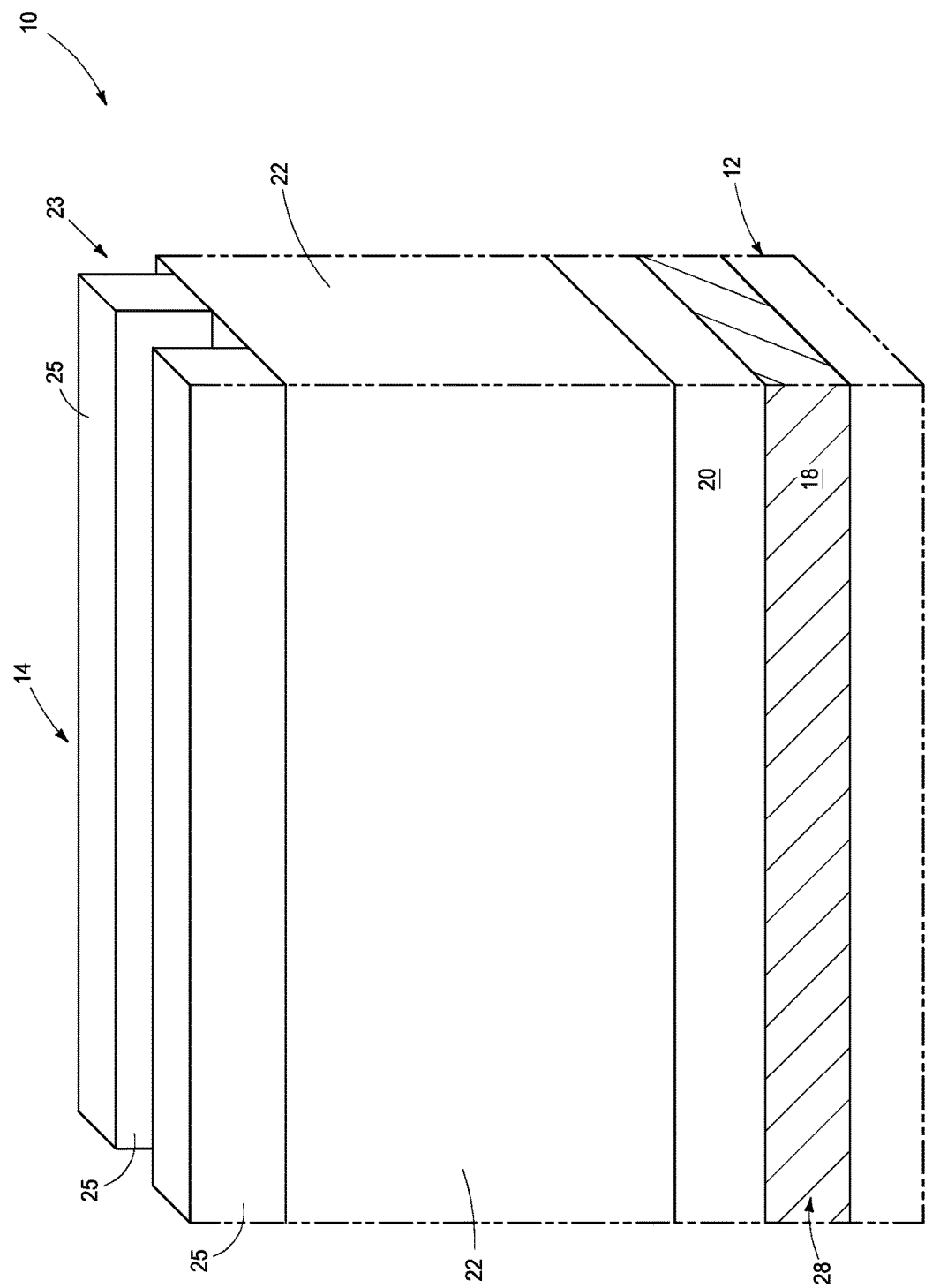
FIG. 3 is a view of the FIG. 2 construction at a processing step subsequent to that shown by FIGS. 1 and 2.

Referring to FIG. 3, and in one embodiment, a first part of a first sacrificial masking step is shown. In the context of this document, a "sacrificial masking step" is a patterning technique using masking material that is patterned over substrate material combined with subsequent removal (e.g., by etching) of substrate material that is uncovered by the masking material, and with at least an uppermost portion of the masking material being sacrificial and thereby ultimately being removed from being over the substrate. The masking material may include a lowest portion that remains as part of the finished circuitry construction. Alternately, all of the sacrificial masking material may be completely removed. For example, construction 10 in FIG. 3 comprises a first sacrificial mask 23 comprising masking material 25 that has been patterned atop substrate material 22/20/18/12. Masking material 25 may comprise photo-imageable or other material with or without one or more other layers of hard-masking or other material. An example technique of forming mask 23 includes photolithographic patterning with or without pitch multiplication.

Figure 4:
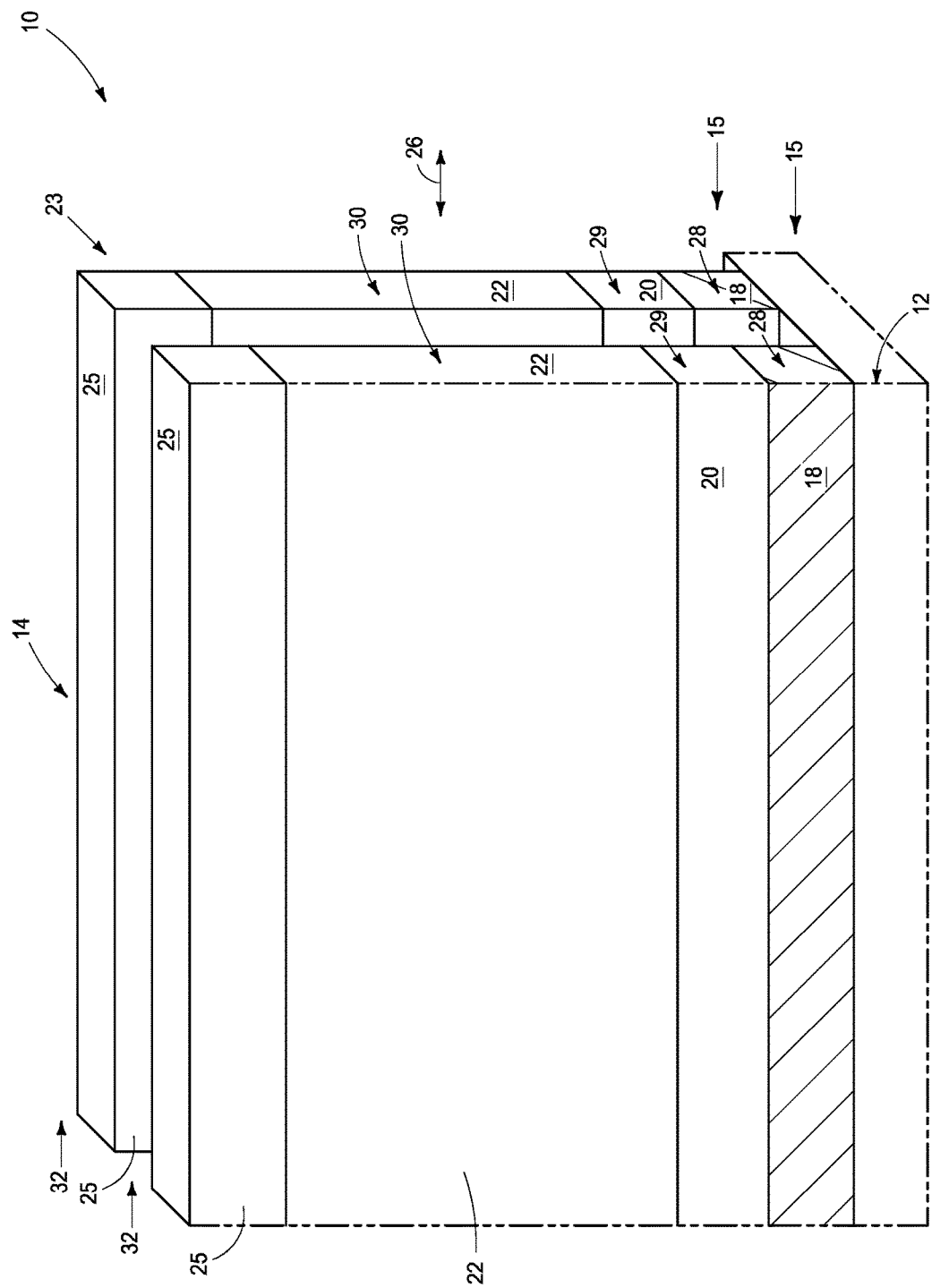
FIG. 4 is a view of the FIG. 3 construction at a processing step subsequent to that shown by FIG. 3.

FIG. 4 shows example completion of the first sacrificial masking step whereby at least some exposed material elevationally inward of mask 23 has been removed. Specifically, FIG. 4 shows that first sacrificial mask 23 has been used to pattern digit line material 18, channel-comprising material 20 there-above, and source/drain-comprising material 22, for example in a first direction 26, to form columns 15 of digit lines 28 within array 14, and having lines 29 of channel-comprising material 20 and lines 30 of source/drain-comprising material 22 there-above. By way of example, such may be conducted using any suitable existing or yet-to-be developed anisotropic etching chemistry or chemistries that etch materials 18, 20, and 22 selectively relative to at least lower portions of masking material 25. In this document, a selective etch or removal is an etch or removal where one material is removed relative to another stated material at a rate of at least 2.0:1. As shown, such has formed trenches 32 that are laterally between digit lines 28 and lines 29, 30 there-above. For simplicity and ease of depiction, only two sets of lines 28/29/30 are shown although thousands, tens of thousands, etc. would likely be formed within array 14 along direction 26. Further, such lines are shown as being straight-linear relative to direction 26 and columns 15, although curved, non-parallel, combination of curved and straight segmented, etc. configurations may be used.

Figure 5:
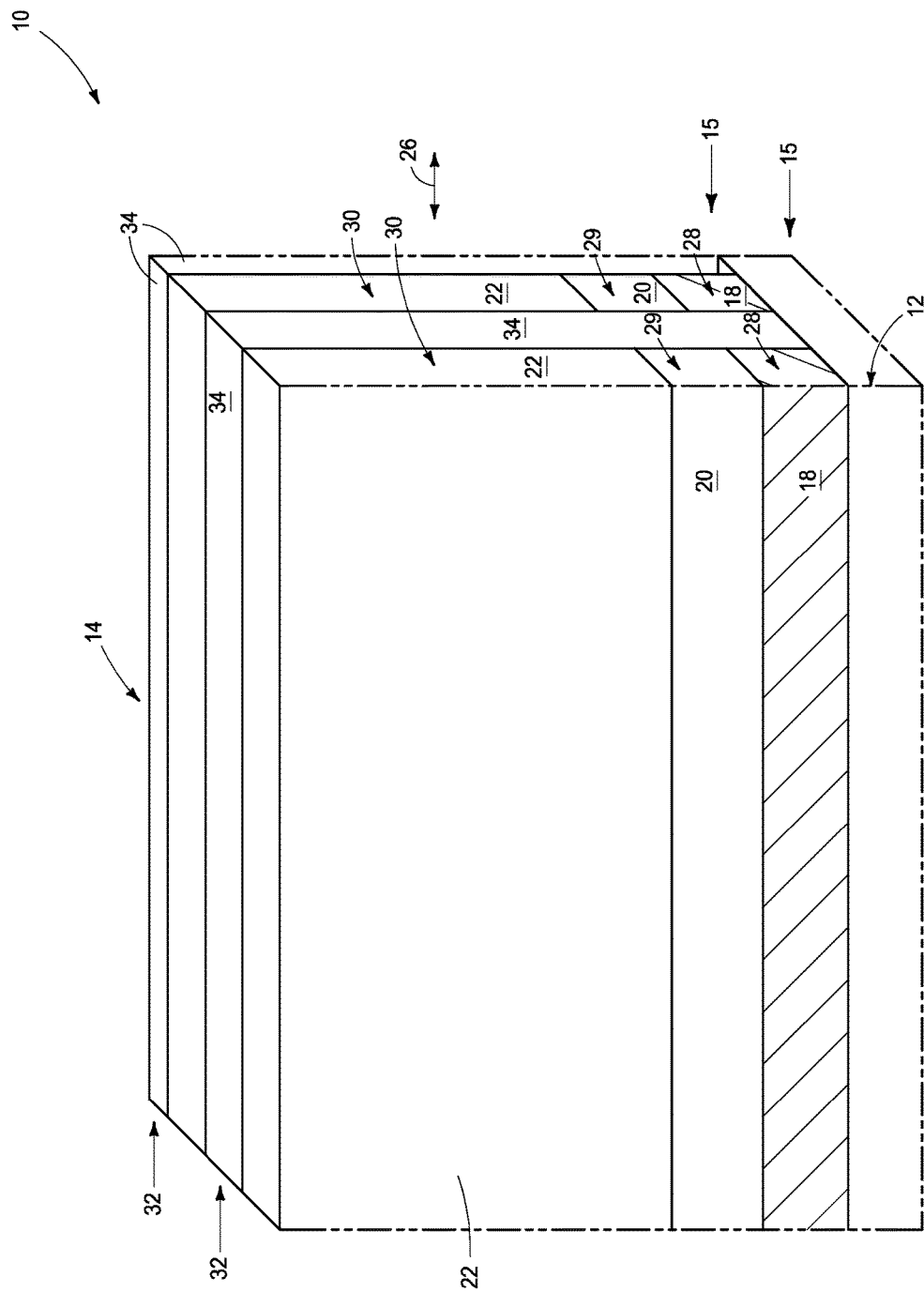
FIG. 5 is a view of the FIG. 4 construction at a processing step subsequent to that shown by FIG. 4.

Referring to FIG. 5, and in one embodiment, all of masking material 25 (not shown) has been removed and first material 34 has been formed in trenches 32. An example technique includes deposition of first material 34 sufficiently to fill and overfill trenches 32, followed by planarizing material 34 back (e.g., by CMP) at least to an uppermost surface of source/drain-comprising material 22. Material 34 is ideally dielectric particularly if such is not entirely sacrificial, with silicon nitride and/or doped or undoped silicon dioxide being examples.

Figure 6:
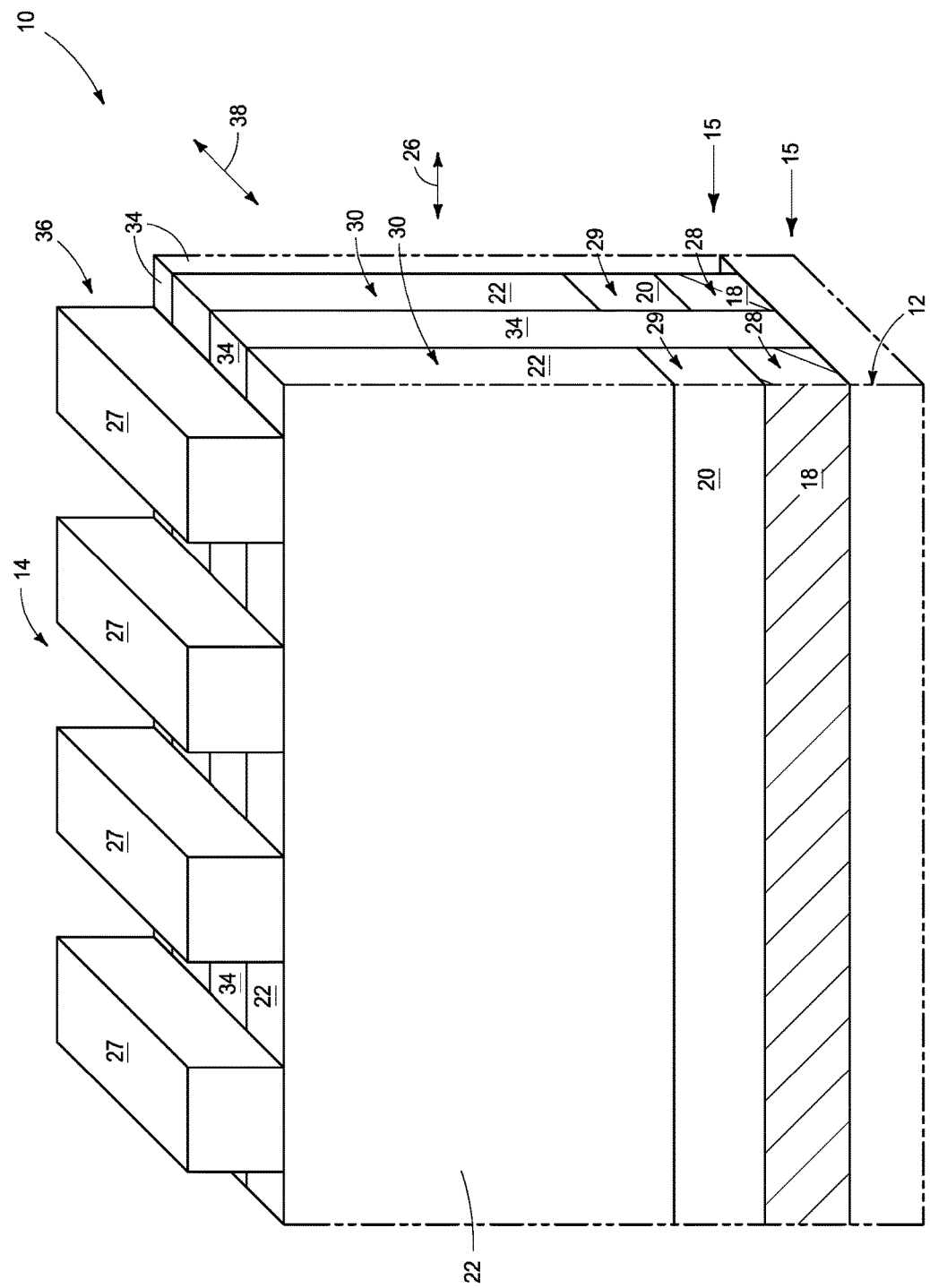
FIG. 6 is a view of the FIG. 5 construction at a processing step subsequent to that shown by FIG. 5.

Referring to FIG. 6, a second sacrificial mask 36 comprising masking material 27 has been formed over materials 22 and 34 and has been patterned in a second direction 38 that is different from first direction 26. The same or different material(s) and/or technique(s) may be used as described above in forming first sacrificial mask 23.

Figure 7:
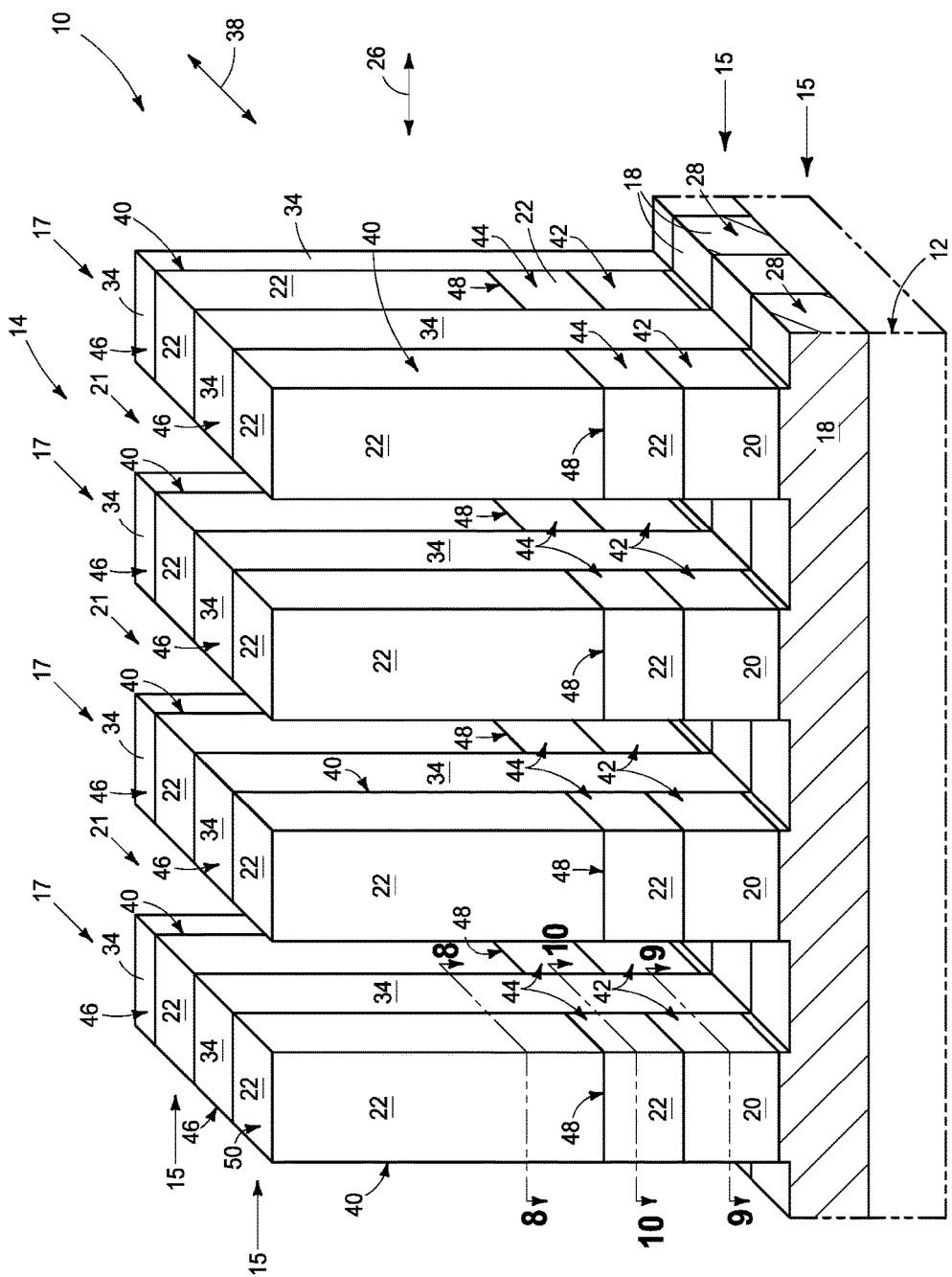
FIG. 7 is a view of the FIG. 6 construction at a processing step subsequent to that shown by FIG. 6.

Referring to FIG. 7, second sacrificial mask 36 (not shown) has been used to pattern channel-comprising material 20 and source/drain-comprising material 22 in second direction 38 to form elevationally-extending pillars 40 (vertical pillars in one embodiment) and comprising individual channels 42 and individual upper source/drain regions 44 of individual transistors of individual memory cells being formed within array 14. First material 34 is laterally between pillars 40. In one embodiment, pillars 40 may be considered as first elevationally-extending pillars with first material 34 forming second elevationally-extending pillars 46, with such first and second elevationally-extending pillars 40 and 46, respectively, alternating relative one another along rows 17 (i.e., being intra-row 17 alternating). Again, for simplicity and ease of depiction, only four rows 17 are shown although thousands, tens of thousands, etc. would likely be formed within array 14 along direction 38, and to result in hundreds of thousands, millions, etc. of pillars 40. Further and regardless, rows 17 are shown as being straight-linear relative to direction 38, although curved, non-parallel, combination of curved and straight segmented, etc. configurations may be used. Construction 10 may be considered as comprising trenches 21 between rows 17. In one embodiment, all of sacrificial masking material 27 (not shown) has been removed from the substrate during and/or after the removal of materials 22, 20, and/or 18.

Accordingly, and in one embodiment, the processing described above relative to FIGS. 1-7 is but one example technique of patterning a digit line material, channel-comprising material, and source/drain-comprising material to form digit lines within the array and to form elevationally-extending pillars comprising individual channels and individual upper source/drain regions of individual transistors of individual memory cells within the array. In one such embodiment, the patterning comprises subtractive etching using more than one sacrificial masking step within the array, and in one embodiment using no more than two sacrificial masking steps within the array.

Alternately or additionally considered, the above-described processing is but one example technique of forming pillars 40 that extend elevationally upward from digit lines 28, with pillars 40 individually comprising an individual channel 42 and an individual upper source/drain region 44 of individual transistors of individual memory cells within array 14. Alternately or additionally considered, the above-described processing is but one example technique of using a second sacrificial mask to pattern channel-comprising material in a second direction that is different from the first direction to cut lines of channel-comprising material above the digit lines into spaced individual channels of individual transistors of individual memory cells within the array.

Figure 10:
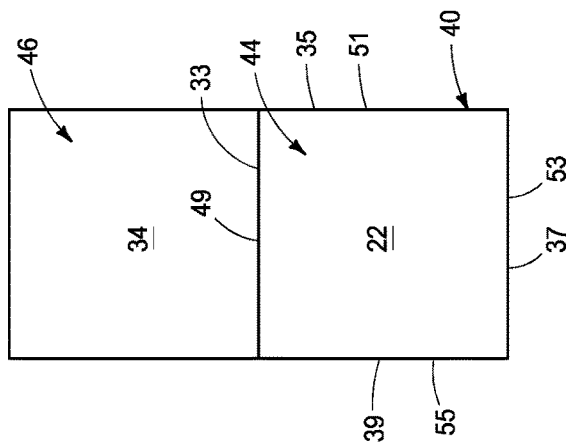
FIG. 10 is a cross-sectional view taken through line 10-10 in FIG. 7.
Figure 9:
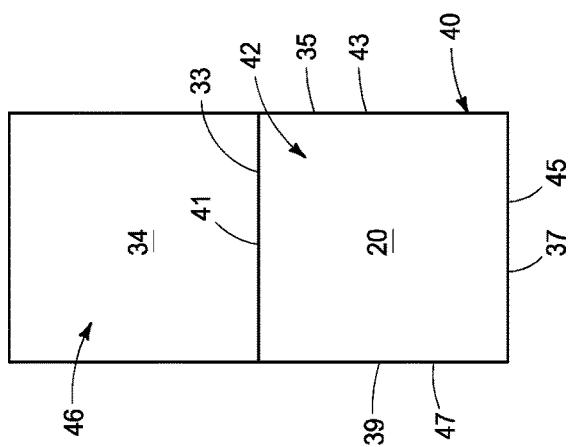
FIG. 9 is a cross-sectional view taken through line 9-9 in FIG. 7.
Figure 8:
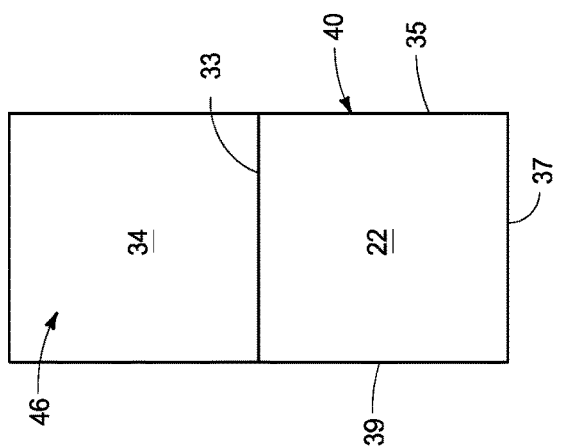
FIG. 8 is a cross-sectional view taken through line 8-8 in FIG. 7.

For purposes of the continuing discussion and referring to FIGS. 8-10, pillars 40 may be considered as having lateral sides 33, 35, 37, and 39. Individual channels 42 (FIG. 9) may be considered as comprising lateral sides 41, 43, 45, and 47 as part of pillar sides 33, 35, 37, and 39, respectively. Upper source/drain regions 44 (FIG. 10) may be considered as comprising lateral sides 49, 51, 53, and 55 which are also a portion of pillar sides 33, 35, 37, and 39, respectively. Pillars 40 and 46 are shown to be of quadrilateral shape in horizontal cross-section, and with four straight lateral sides. Alternate shapes including fewer, more, non-straight, and/or curved lateral sides may be used.

Source/drain regions 44 may be considered as comprising tops 48 (FIG. 7) and pillars 40 may be considered as comprising tops 50 (FIG. 7). In one embodiment, pillars 40 are formed to be conductive from upper source/drain regions 44 to tops 50 of pillars 40 (e.g., whereby upper source/drain region 44 effectively extends elevationally upward to pillar tops 50 thereby not having a pillar-internal top 48). In one embodiment, pillars 40 are formed to be non-conductive from tops 48 to pillar tops 50. In one such embodiment, pillars 40 are formed to be insulative from tops 48 to pillar tops 50 and in another such embodiment are formed to be semiconductive from tops 48 to pillar tops 50.

An access line is formed laterally across and operatively laterally adjacent a lateral side of the individual transistor channels (e.g., at least one of channel sides 49, 51, 53, and 55 in the depicted embodiment). Where so there-adjacent, such comprises a portion of the access line that effectively forms an access gate for the individual transistors. The access lines may individually completely encircle (not shown) respective individual transistor channels or may only be over a portion of the circumference of such channels, for example only being over opposing lateral sides of the transistor channels. One example method of forming access lines is described with reference to FIGS. 11-15.

Figure 11:
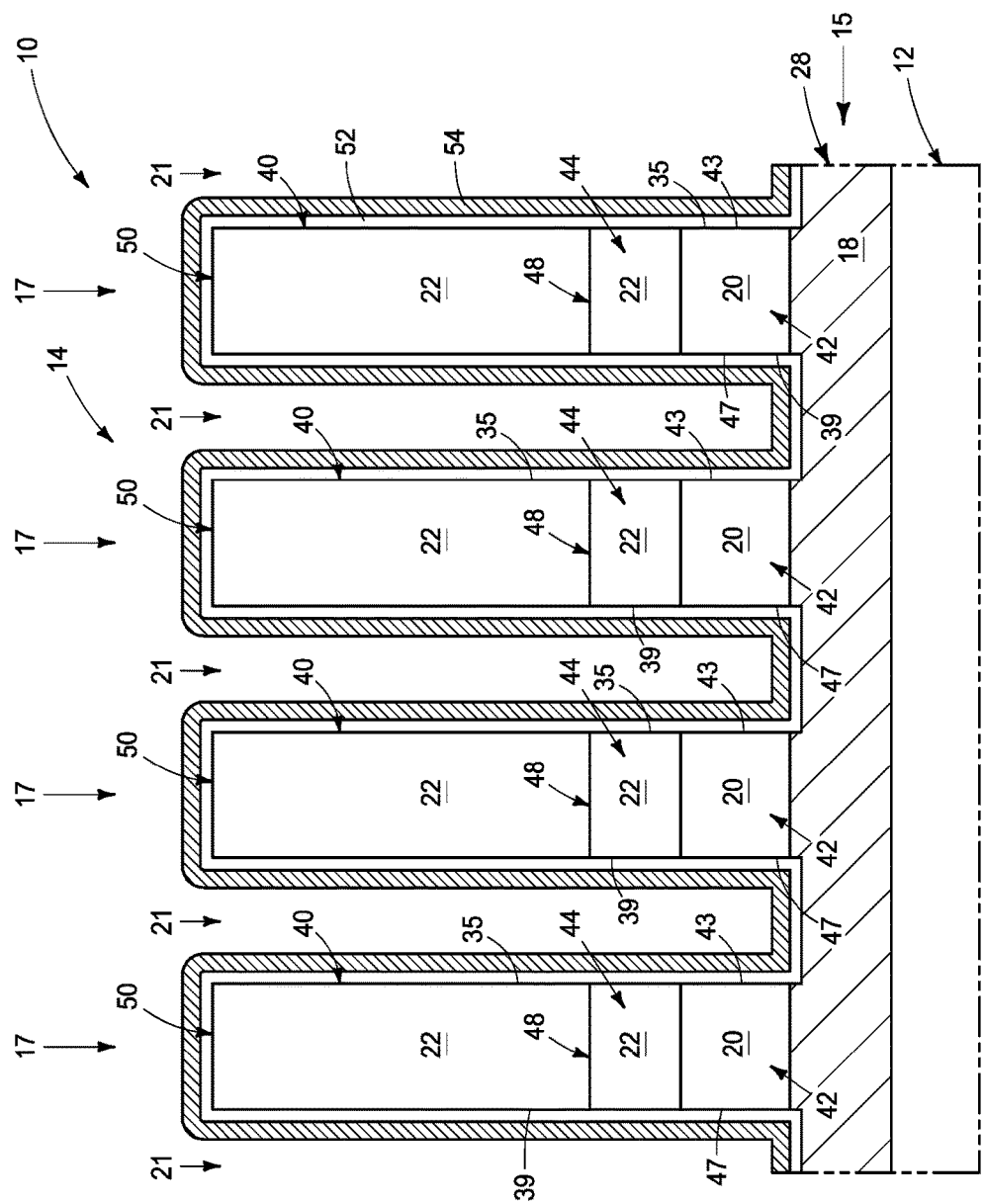
FIG. 11 is a front elevational view of the FIG. 7 construction at a processing step subsequent to that shown by FIG. 7.

Referring to FIG. 11, gate insulator 52 (e.g., silicon dioxide, silicon nitride, high-k dielectric, ferroelectric material, etc.) has been formed over pillar tops 50 and laterally across a pair of first laterally-opposing sides 35, 39 of individual pillars 40 operatively laterally adjacent a pair of first laterally-opposing sides 43, 47 of individual channels 42 within array 14 and between laterally-row-adjacent pillars 40 (e.g., between inter-row-adjacent pillars). Access gate material 54 (e.g., TiN) has been formed over gate insulator 52, including over pillar tops 50, over first laterally-opposing sides 35, 39 of pillars 40 and over a pair of first laterally-opposing sides 43, 47 of channels 42, and between laterally-row-adjacent pillars 40.

Figure 12:
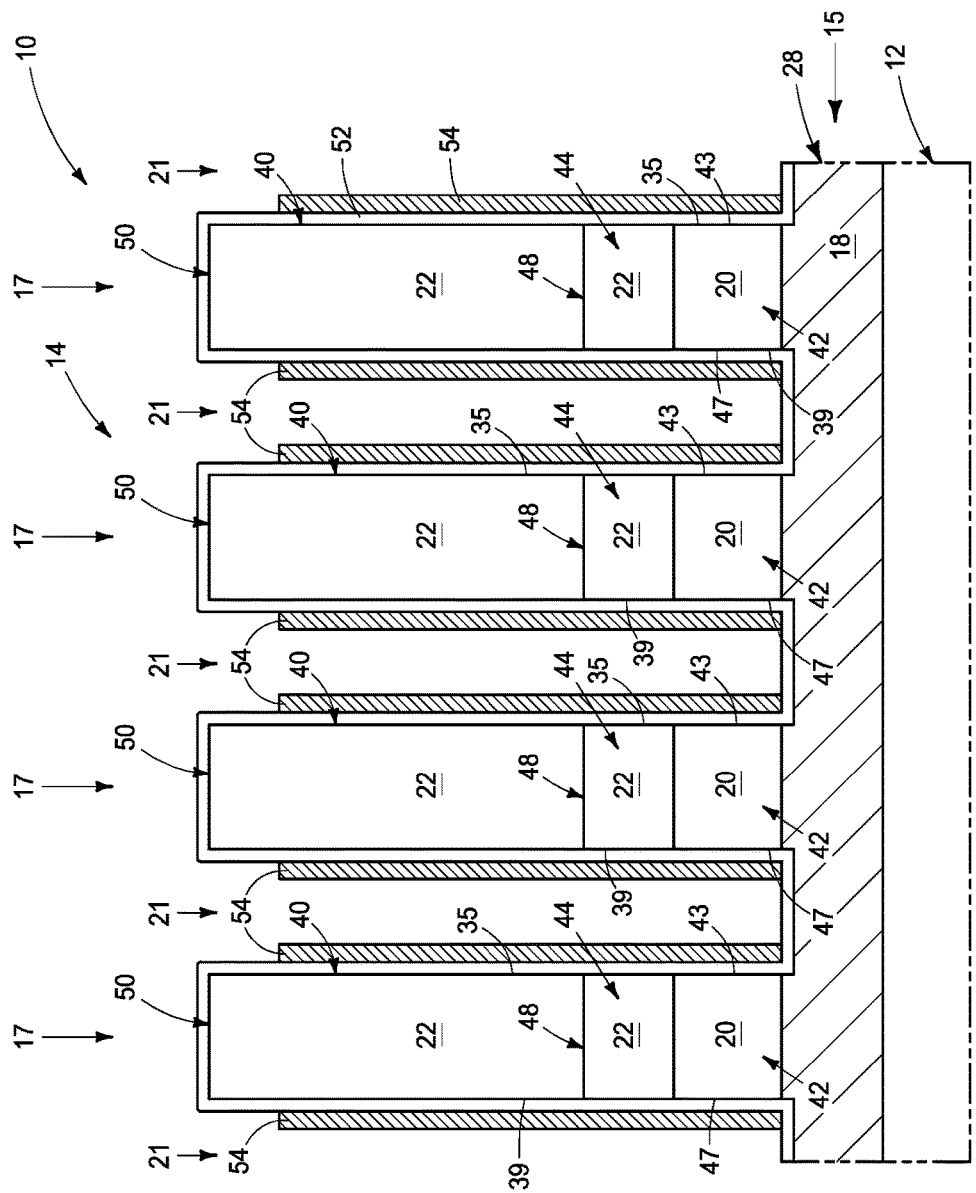
FIG. 12 is a view of the FIG. 11 construction at a processing step subsequent to that shown by FIG. 11.

Referring to FIG. 12, and in one embodiment, access gate material 54 has been subjected to maskless anisotropic etching (i.e., maskless at least within all of array 14), and which in one embodiment is conducted selectively relative to gate insulator 52, to remove material 54 from being over pillar tops 50 and from being interconnected between laterally-row-adjacent pillars 40. Gate insulator 52 may also be so-removed (not shown) during or after such maskless anisotropic etching of access gate material 54.

Figure 13:
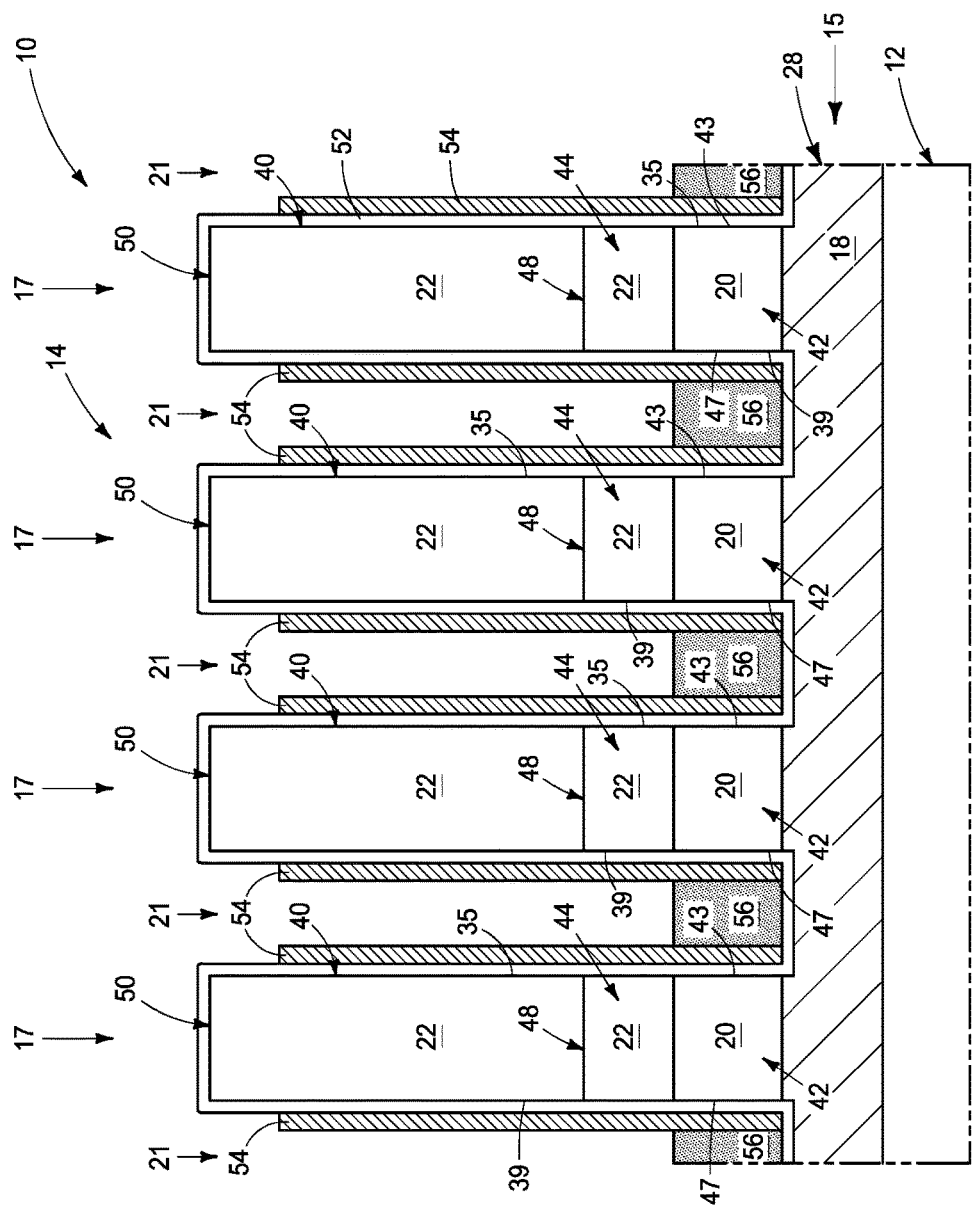
FIG. 13 is a view of the FIG. 12 construction at a processing step subsequent to that shown by FIG. 12.

Referring to FIG. 13, at least lower portions of trenches 21 between rows 17 of pillars 40 have been plugged with sacrificial material 56 (e.g., photoresist). Such may be conducted by deposition of material 56 followed by a timed etch-back thereof as shown.

Figure 14:
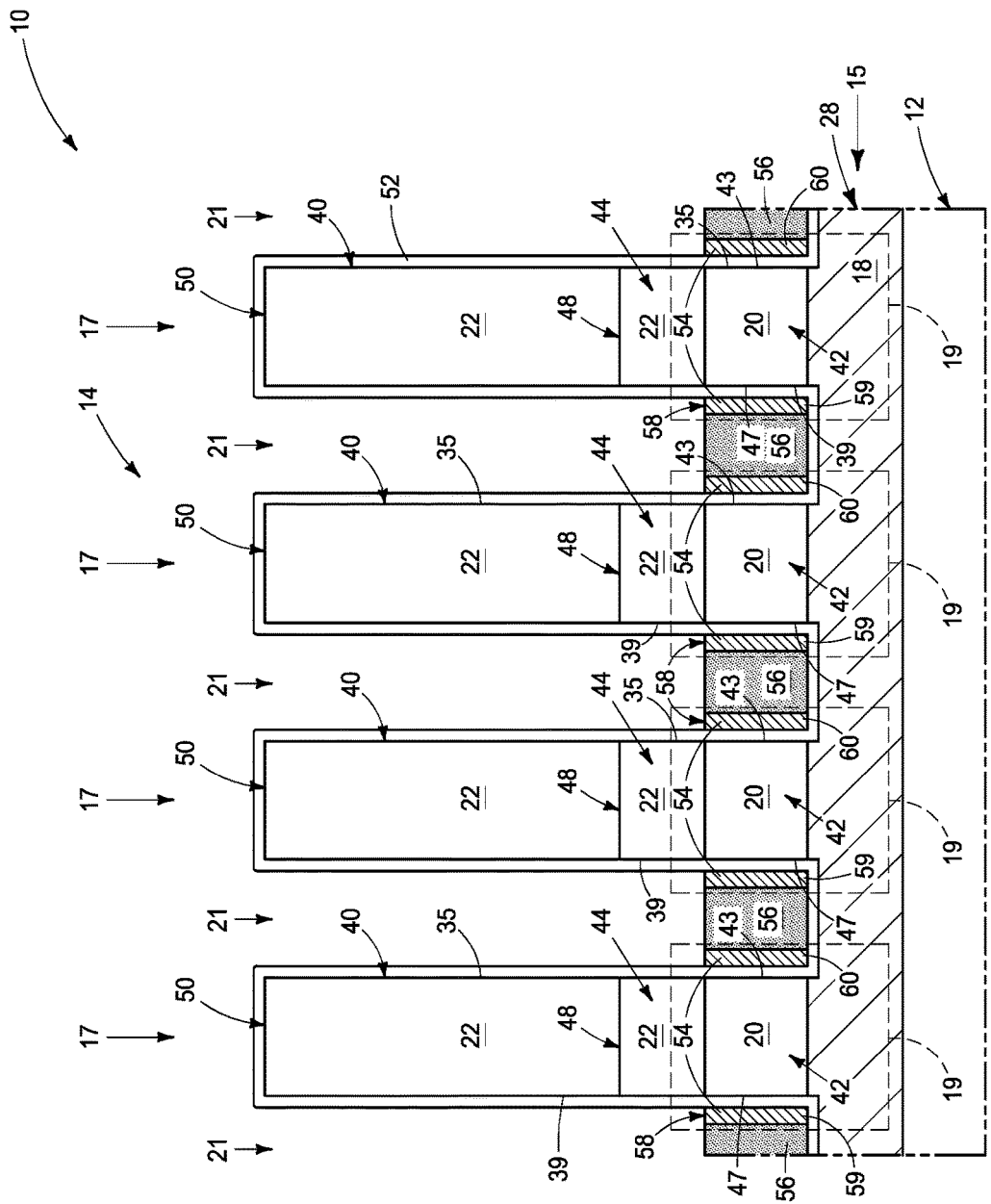
FIG. 14 is a view of the FIG. 13 construction at a processing step subsequent to that shown by FIG. 13.
Figure 15:
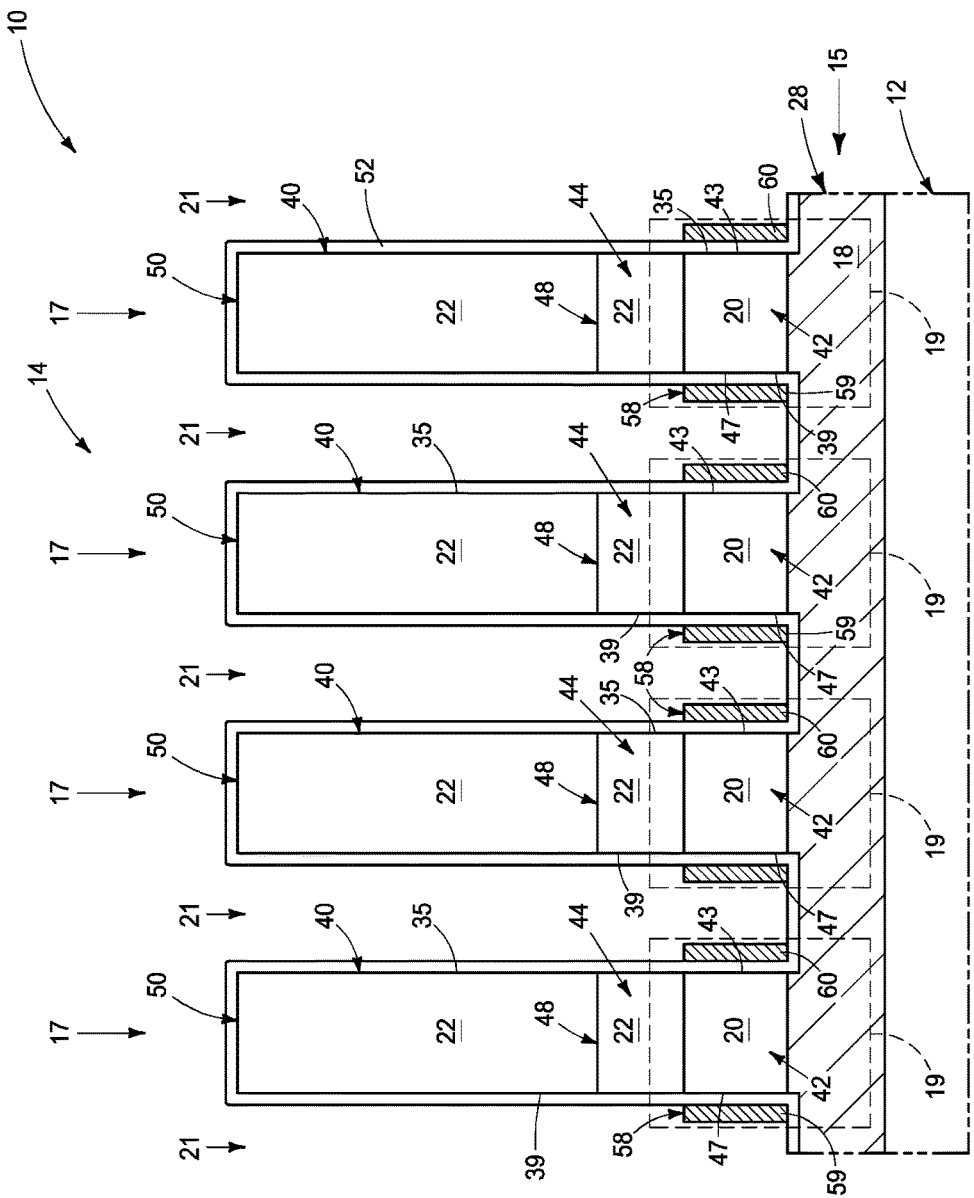
FIG. 15 is a view of the FIG. 14 construction at a processing step subsequent to that shown by FIG. 14.

Referring to FIG. 14, access gate material 54 has been removed back (e.g., by timed etching), and in one embodiment as shown selectively relative to sacrificial material 56 and gate insulator 52. In the depicted embodiment, such has resulted in the formation of an access line 58 that is laterally across and operatively laterally adjacent a lateral side of individual transistor channels 42, thus forming individual transistors 19. Those portions of individual access lines 58 where so there-adjacent effectively forms an access gate for individual transistors 19. Respective uppermost portions of digit lines 28 that are immediately-below individual channels 42 may function as individual lower source/drain regions for individual transistors 19. In one embodiment and as shown, individual access lines 58 are in the form of access line pairs 59, 60 that are laterally across first laterally-opposing sides 35, 39 of pillars 40 operatively laterally adjacent first laterally-opposing sides 43, 47 of individual channels 42 within array 14. In one embodiment, access line pairs 59, 60 are in respective individual row lines 17 and interconnect the transistors in that row. In one embodiment and in accordance with the above-described processing, the maskless anisotropic etching of the access gate material is conducted in at least two time-spaced etching steps (e.g., FIG. 12 and FIG. 14), and in one embodiment wherein a lower portion of trenches 21 between rows 17 of pillars 40 is plugged with sacrificial material 56 during a later (FIG. 14) of the maskless anisotropic etching steps. An example lateral thickness for each of pairs 59 and 60 is 30 to 75 Angstroms. FIG. 14 shows only four transistors 19 along a column-side of array 14 although likely thousands, tens of thousands, etc. transistors would extend along individual columns and individual rows resulting in hundreds of thousands, millions, etc. transistors with array 14. FIG. 15 shows subsequent removal of sacrificial material 56 (not shown).

In one embodiment, respective access line pairs 59 and 60 of an individual access line 58 may be electrically coupled (in one embodiment directly electrically coupled) relative to each other outside of array 14 within peripheral area 16 (with peripheral area 16 only being show in FIG. 1) in another sacrificial masking step or otherwise. In this document, regions/materials/components are "electrically coupled" relative one another if in normal operation electric current is capable of continuously flowing from one to the other, and does so predominately by movement of subatomic positive and/or negative charges when such are sufficiently generated. Another electronic component may be between and electrically coupled to the regions/materials/components. In contrast, when regions/materials/components are referred to as being "directly electrically coupled", no intervening electronic component (e.g., no diode, transistor, resistor, transducer, switch, fuse, etc.) is between the directly electrically coupled regions/materials/components.

Figure 16:
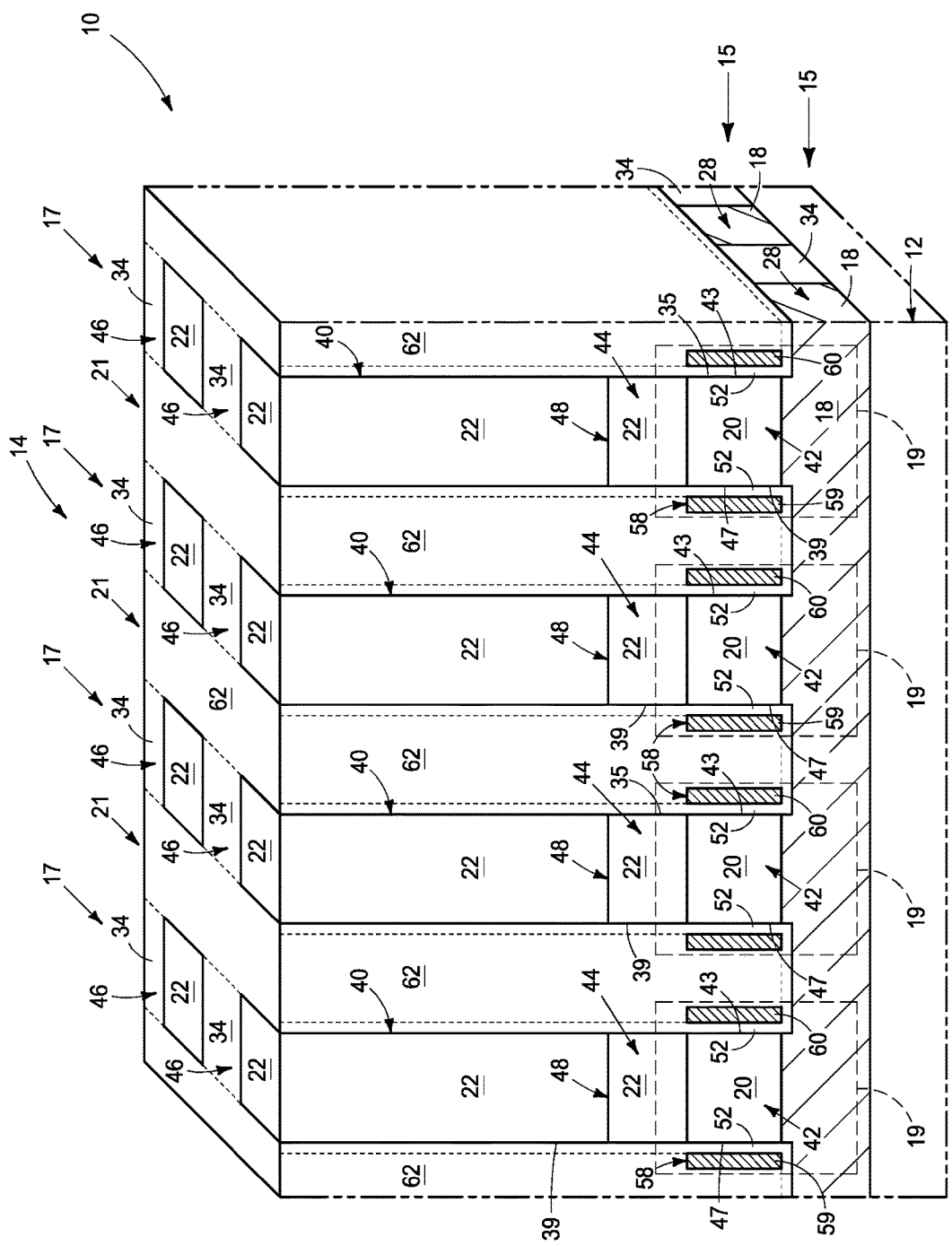
FIG. 16 is a perspective view of the FIG. 15 construction at a processing step subsequent to that shown by FIG. 15.

Referring to FIG. 16, second material 62 has been formed in trenches 21. Material 62 may be of any suitable composition, with at least a lower portion thereof being insulative if material 62 is not entirely sacrificial. If gate insulator 52 remains over bases of trenches 21 between row-adjacent access lines 58 and/or above access lines 58, gate insulator 52 effectively becomes part of second material 62 and may be of the same or different composition as original second material 62, and as shown in FIG. 16 being of the same composition. In one embodiment, first material 34 and second material 62 are formed to be of the same composition relative one another, and in another embodiment are formed to be of different composition relative one another.

Capacitors are ultimately formed that individually have one of their capacitor electrodes directly against a lateral side of an upper source/drain region of one of the individual transistors of the individual memory cells within the array. In one embodiment, the one capacitor electrodes individually are formed directly against less than all of the lateral side of the respective upper source/drain region, and in one embodiment are formed directly against less than half of the lateral side of the respective upper source/drain region. In one embodiment, the forming of capacitors forms individual of the one capacitor electrodes directly against first laterally-opposing sides, and in one such embodiment no more than two laterally-opposing sides, of the individual upper source/drain regions. In one embodiment, the individual upper source/drain regions may be considered as having completely encircling peripheral lateral side surfaces, and with the individual one capacitor electrodes being directly against all of the completely encircling peripheral lateral side surfaces of the individual upper source/drain regions. Two example embodiments of forming capacitors are next described with reference to FIGS. 17-24.

Figure 17:
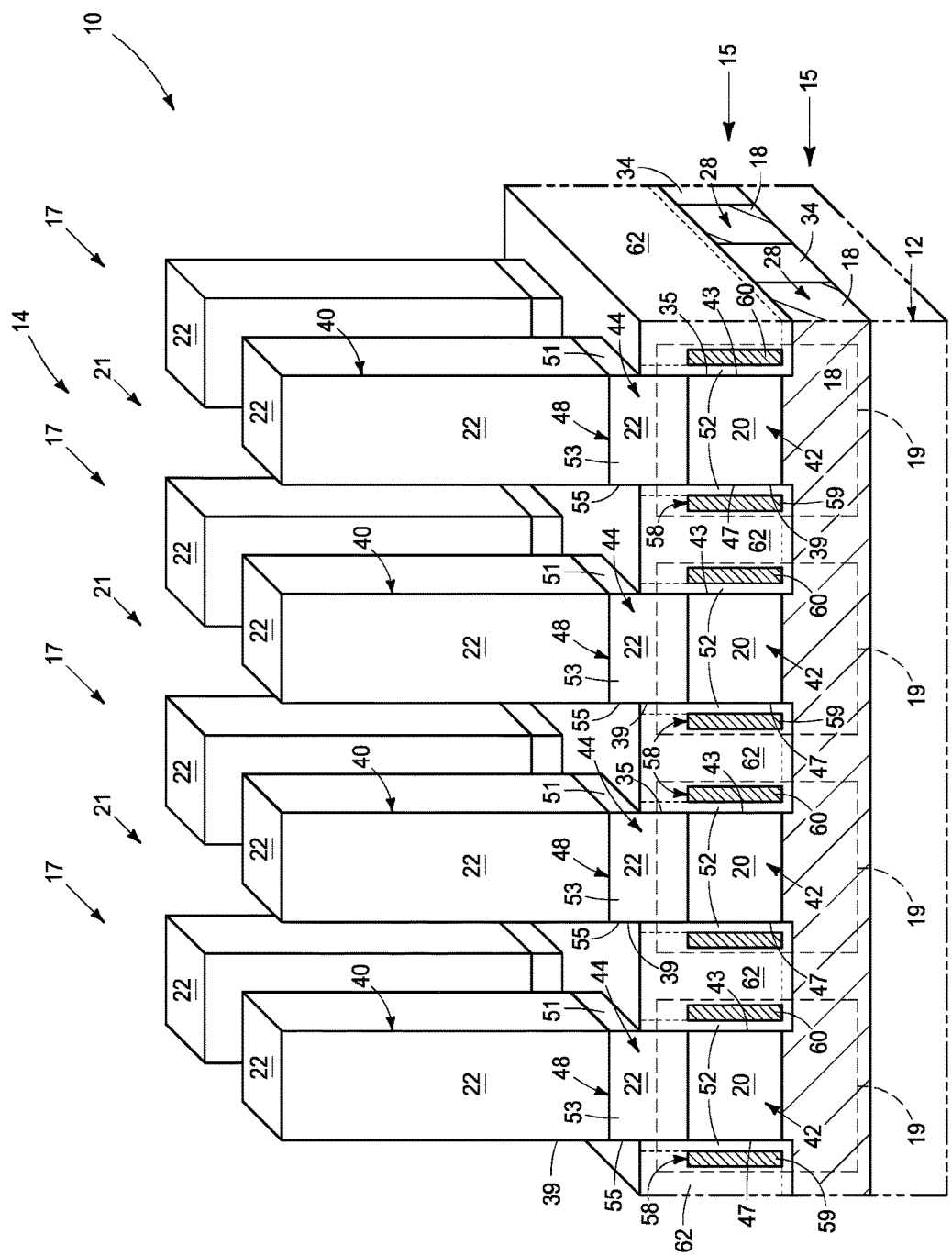
FIG. 17 is a view of the FIG. 16 construction at a processing step subsequent to that shown by FIG. 16.

Referring to FIG. 17, first material 34 and second material 62 have been removed sufficiently to expose encircling peripheral lateral sides 49, 51, 53, and 55 of individual upper source/drain regions 44 (side 49 not be visible in FIG. 17).

Figure 18:
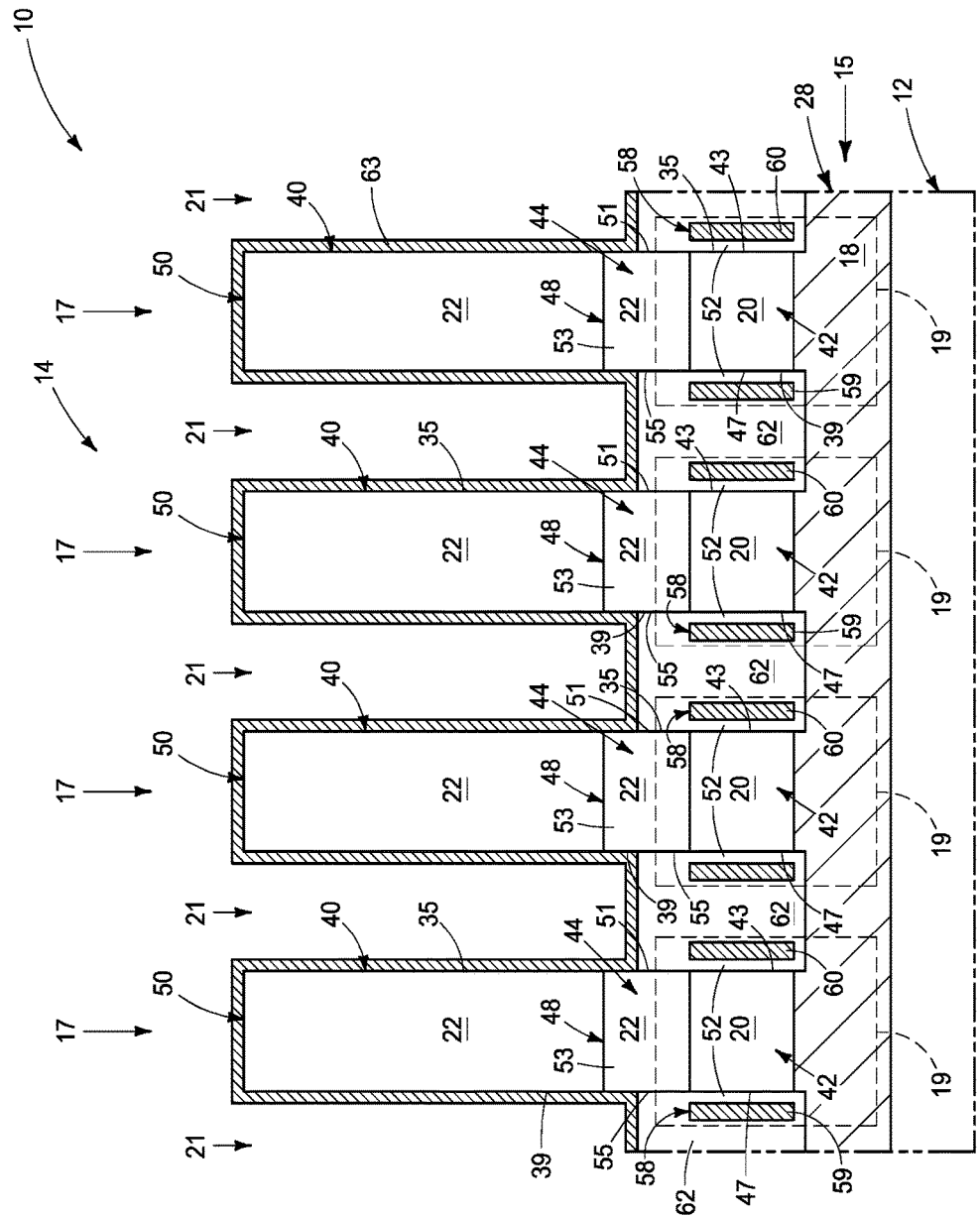
FIG. 18 is a front elevational view of the FIG. 17 construction at a processing step subsequent to that shown by FIG. 17, and is taken through line 18-18 in FIG. 19.
Figure 19:
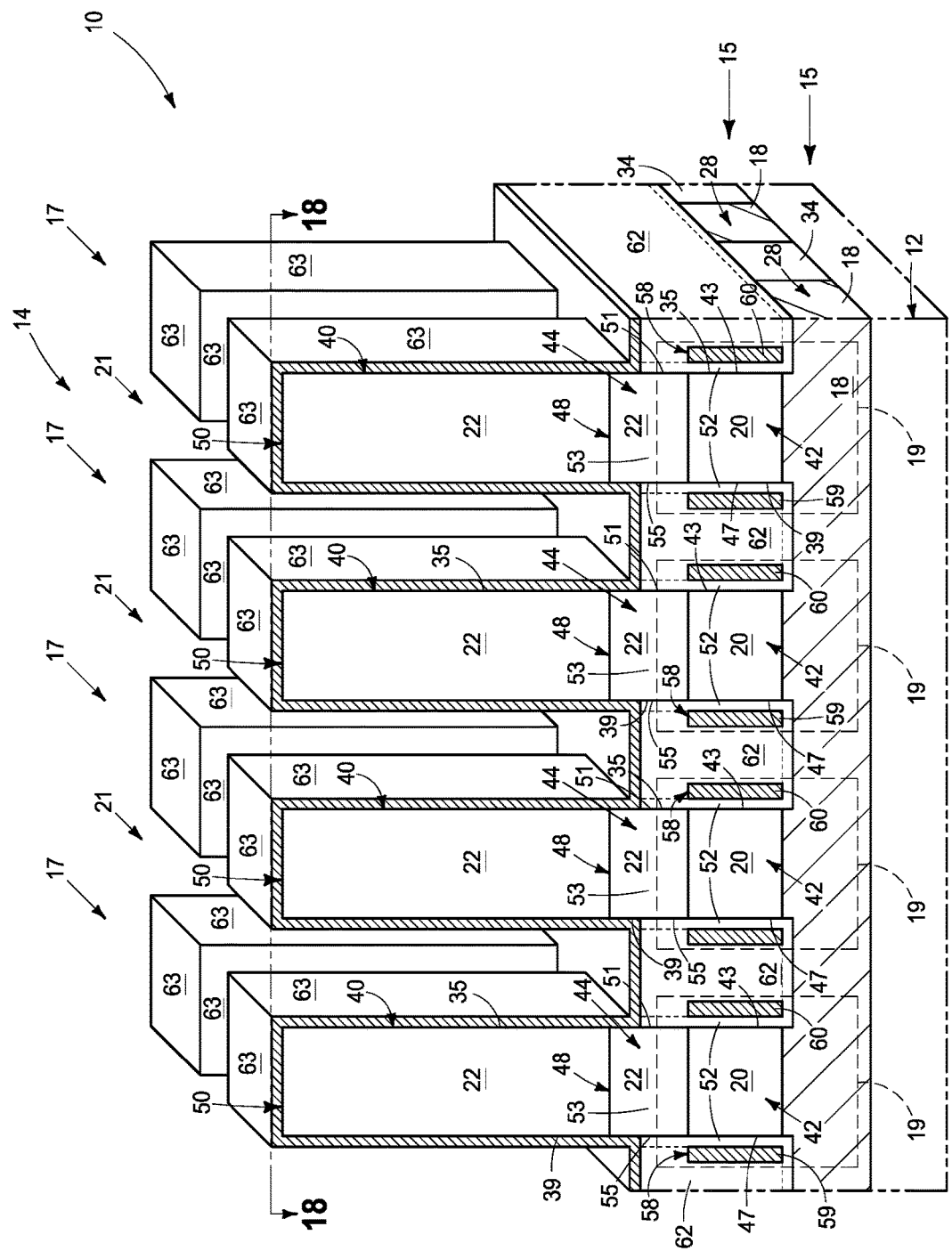
FIG. 19 is a perspective view of FIG. 18.

Referring to FIGS. 18 and 19, first capacitor electrode-comprising material 63 (e.g., TiN) has been formed over tops 50 and first laterally-opposing sides 35, 39 of pillars 40 directly against a pair of first laterally-opposing sides 51, 55 of individual upper source/drain regions 44 and between laterally-row-adjacent pillars 40. In one embodiment and as shown, first capacitor electrode-comprising material 63 completely encircles and is directly against all of encircling peripheral lateral sides 49, 51, 53, and 55 of individual upper source/drain regions 44 within array 14 (side 49 not be visible in FIGS. 18 and 19). An example thickness for material 63 is 25 to 50 Angstroms.

Figure 20:
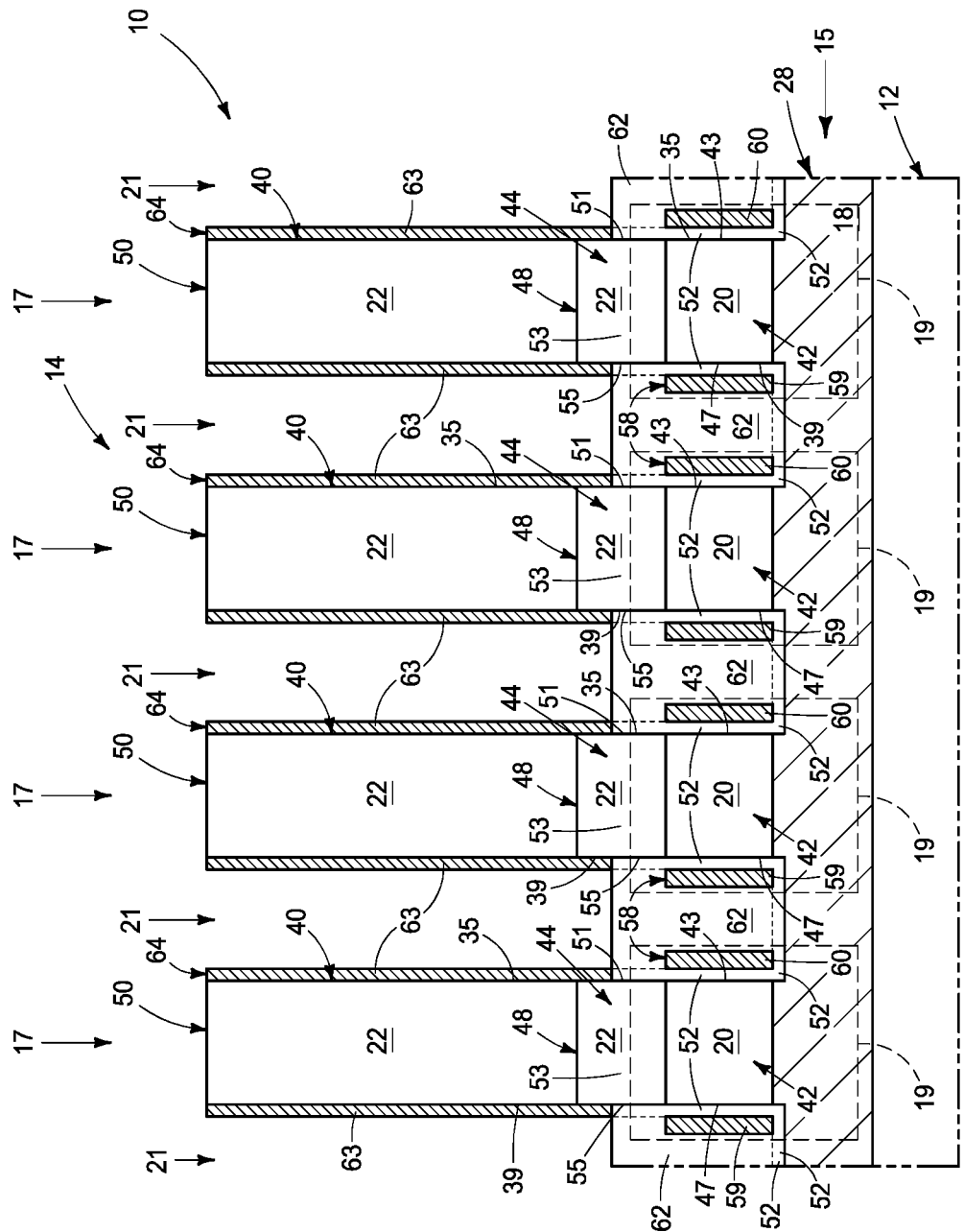
FIG. 20 is a view of the FIG. 18 construction at a processing step subsequent to that shown by FIG. 18.
Figure 21:
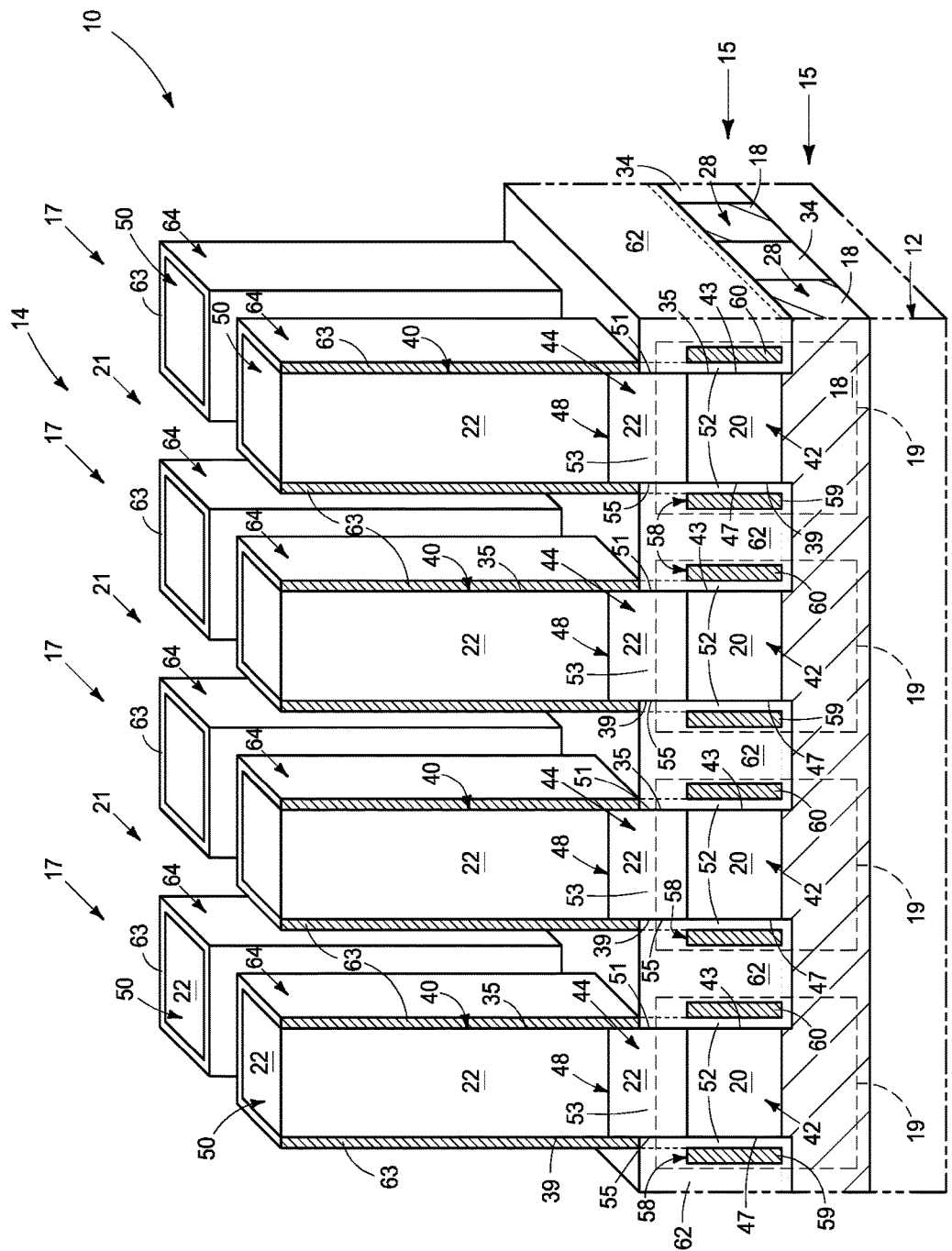
FIG. 21 is a perspective view of the FIG. 20 construction.

Referring to FIGS. 20 and 21, and in one embodiment, maskless anisotropic etching (i.e., maskless at least within all of array 14) has been conducted of first capacitor electrode-comprising material 63 to remove it from being over pillar tops 50 and from being interconnected between laterally-row-adjacent pillars 40. Thereby, and in one embodiment, first capacitor electrodes 64 have been formed and that completely encircle and are directly against all of the encircling peripheral lateral sides of the individual upper source/drain regions within the array.

Figure 22:
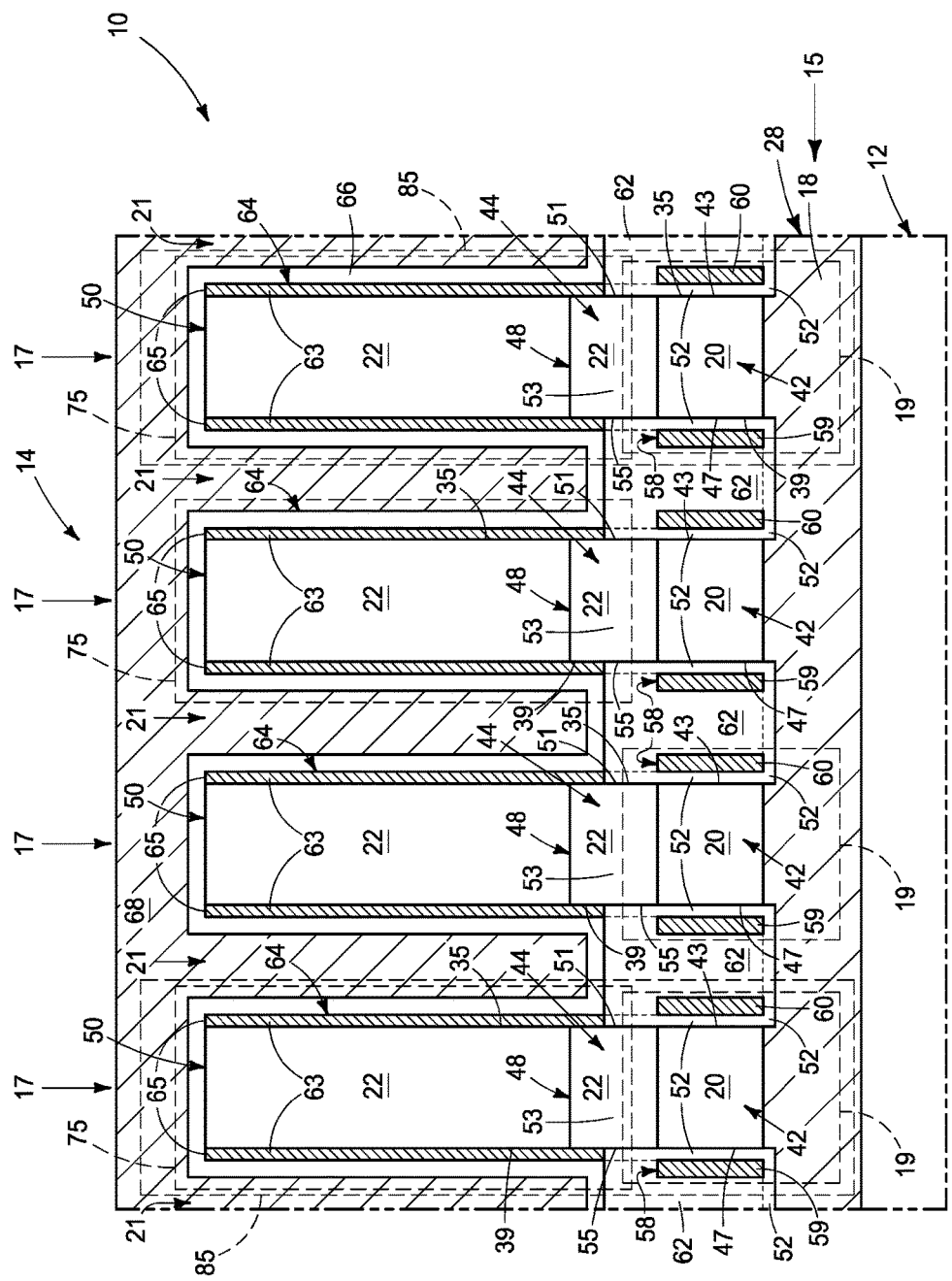
FIG. 22 is a front elevational view of the FIG. 21 construction at a processing step subsequent to that shown by FIG. 21.

Referring to FIG. 22, a capacitor insulator 66 has been formed over first capacitor electrodes 64 and a second capacitor electrode 68 has been formed over capacitor insulator 66 within array 14, thus forming individual capacitors 75 and individual memory cells 85. In one embodiment and as shown, second capacitor electrode 68 is singular and common to capacitors 75 within array 14. Material of second capacitor electrode 68 may be of the same or different composition as first capacitor electrode-comprising material 63. In one embodiment and as shown, capacitor insulator 66 completely encircles individual first capacitor electrodes 64, and second capacitor electrode 68 completely encircles capacitor insulator 66 about pillars 40 within array 14.

Example capacitor insulator materials include $SiO_2$, $Si_3N_4$, and/or high-k dielectrics and whereby the capacitors are not volatile. Alternately in other example embodiments, capacitor insulator 66 comprises programmable material such that the capacitors are formed to be non-volatile and programmable into at least two different magnitude capacitive states (e.g., whereby the programmable material is both sufficiently thick and remains insulative in the different states such that a current sufficient to erase a stored state does not flow there-through at operating voltages). Example such programmable materials include ferroelectric materials, conductive bridging RAM (CBRAM) materials, phase change materials, and resistive RAM (RRAM) materials, with ferroelectrics believed to be ideal. Example ferroelectric material include ferroelectrics that have one or more of transition metal oxide, zirconium, zirconium oxide, niobium, niobium oxide, hafnium, hafnium oxide, lead zirconium titanate, and barium strontium titanate, and may have dopant therein which comprises one or more of silicon, aluminum, lanthanum, yttrium, erbium, calcium, magnesium, strontium, and a rare-earth element. In one embodiment, capacitor insulator 66 comprises dielectric material such that the capacitors are volatile. For example, such can comprise one or more of non-programmable dielectric materials such as silicon dioxide, silicon nitride, aluminum oxide, high-k dielectrics, etc. whereby no charge is retained in material 66 upon removal or sufficient reduction of voltage/potential from one or both of the two capacitor electrodes of the capacitor. Non-volatile programmable capacitors may have a capacitor insulator that has a suitable combination of programmable material(s) and non-programmable material(s). Regardless, an example thickness for capacitor insulator 66 is 30 to 100 Angstroms.

Any materials that may be doped with suitable conductivity modifying dopants (e.g., materials 20 and 22) to provide a selected conductivity may be so doped at time of deposition and/or subsequently.

Any other attribute(s) or aspect(s) as described herein and/or shown may be used in the embodiments described above with reference to FIGS. 1-22.

Figure 23:
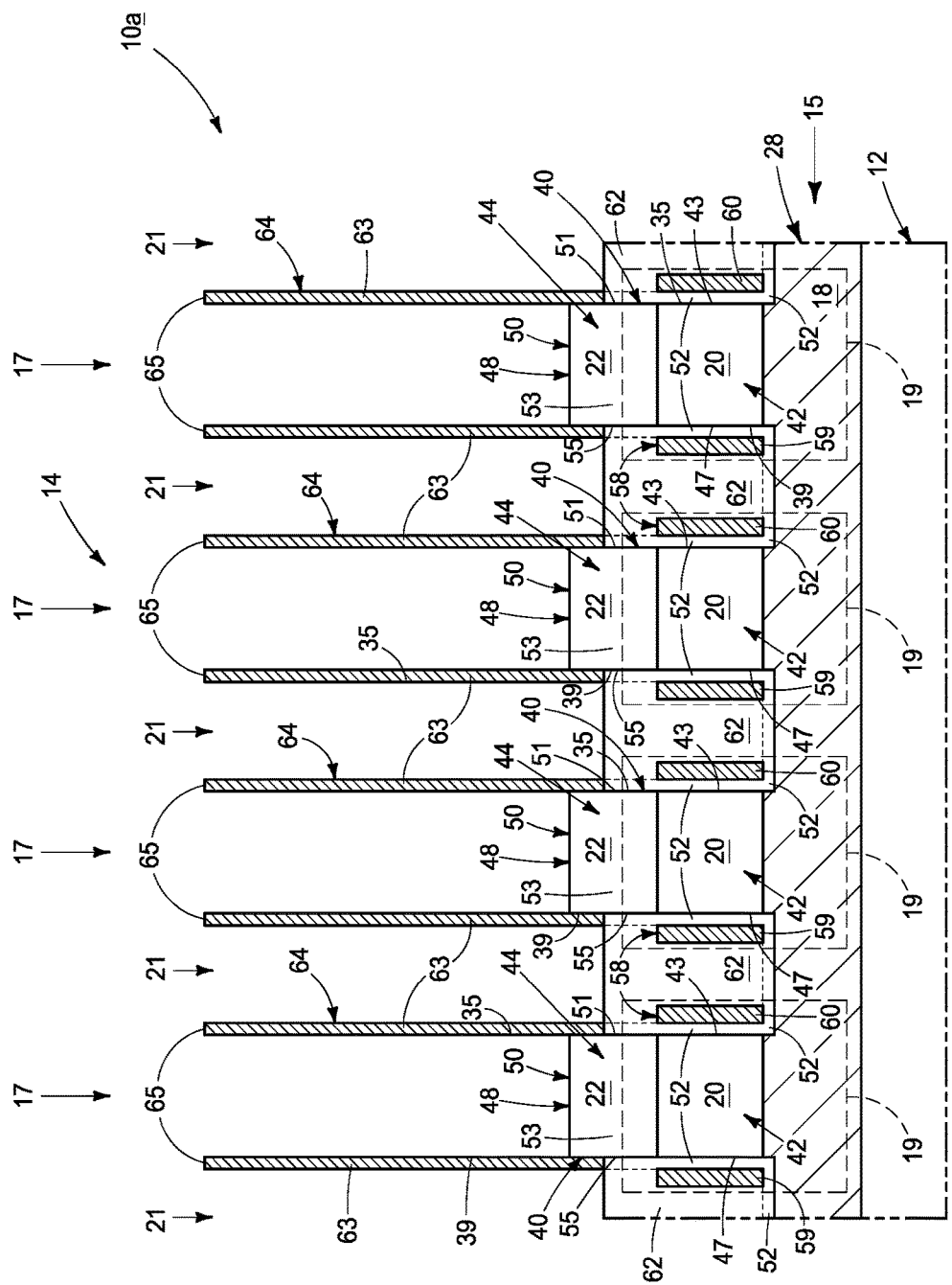
FIG. 23 is a diagrammatic front elevational view of a substrate construction in process in accordance with an embodiment of the invention.

FIGS. 17-22 depict an embodiment wherein first capacitor electrodes 64 have been formed to have their respective tops 65 planar and elevationally coincident with a planar top 50 of their respected encircled pillars 40. Alternately and by way of example, the first capacitor electrodes may be formed to have their respective tops not be elevationally coincident with the tops of their respective encircled pillars, for example as is next-described with respect to an alternate embodiment construction 10a shown in FIGS. 23 and 24. Like numerals from the above-described embodiments have been used where appropriate, with some construction differences being indicated with the suffix "a" or with different numerals. Construction 10a in FIG. 23 shows processing conducted immediately subsequent to FIGS. 20 and 21 alternate to that shown by FIG. 22. Specifically, material 22 of pillars 40, after forming first capacitor electrodes 64, has been removed selectively relative to first capacitor electrodes 64 before forming the capacitor insulator. FIG. 23 shows removal of material 22 back to tops 48 of upper source/drain regions 44. Alternately in one embodiment, some upper material of upper source/drain regions 44 may be removed (not shown) as long as some lateral side surface thereof remains laterally against the respective first capacitor electrodes 64. Alternately, material 22 of pillars 40 may not be removed downward to tops 48 (not shown) of source/drain regions 44. In one embodiment where material 22 of pillar 40 is selectively removed, such removing removes more than half of all of pillar material 20/22 away before forming the capacitor insulator.

Figure 24:
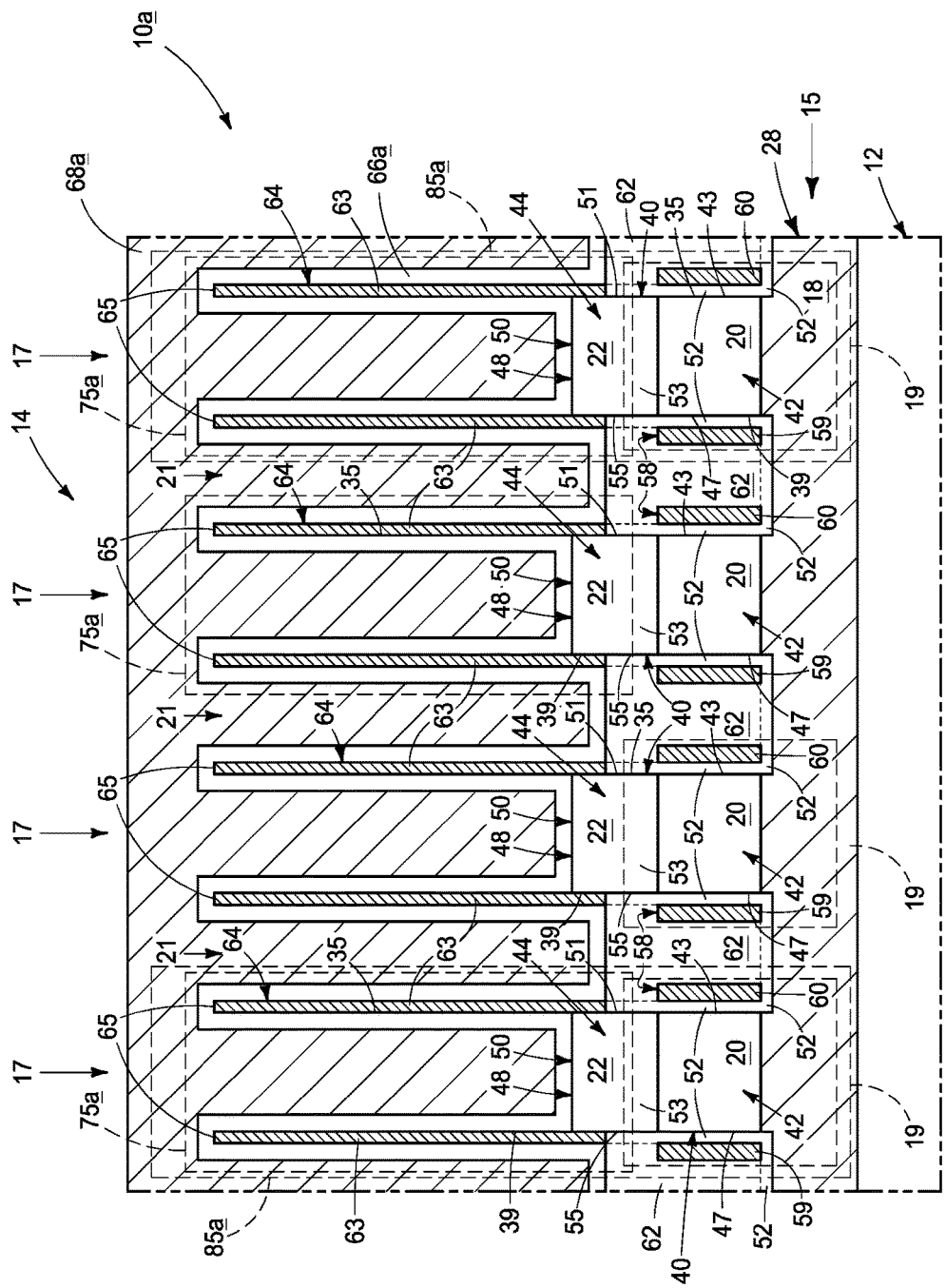
FIG. 24 is a view of the FIG. 23 construction at a processing step subsequent to that shown by FIG. 23.

Regardless, FIG. 24 shows subsequent processing wherein capacitor insulator 66a and second capacitor electrode 68a have been formed laterally over radially internal sides and radially external sides of a majority of first capacitor electrodes 64, thus forming capacitors 75a and memory cells 85a. FIG. 24 shows an example embodiment wherein first capacitor electrode 64 has been formed to have its top 65 be higher than top 50 of its encircled pillar 40. In one embodiment and as shown, capacitor insulator 66a is formed directly against tops 48 of encircled individual source/drain regions 44. In one embodiment and as shown, capacitor insulator 66a is formed laterally over all of the radially external sides of individual first capacitor electrodes 64 and laterally over only some of the radially internal sides of individual first capacitor electrodes 64. In one embodiment and as shown, FIGS. 23 and 24 may be considered as forming first capacitor electrode 64 in the form of a cylinder having radially inner sides and radially outer sides. Capacitor insulator 66a is over the radially outer sides and the radially inner sides of first capacitor electrode cylinder 64. Second capacitor electrode 68a is over capacitor insulator 66a and over the radially outer sides and the radially inner sides of the first capacitor electrode cylinder 64. Any other attribute(s) or aspect(s) as described herein and/or shown may be used.

The above embodiments described with respect to FIGS. 1-22 are example method embodiments that are devoid of etching material of the pillar after forming the first capacitor electrodes, whereas the embodiment described above with respect to FIGS. 23 and 24 etches material of the pillar after forming the first capacitor electrodes.

Figure 25:
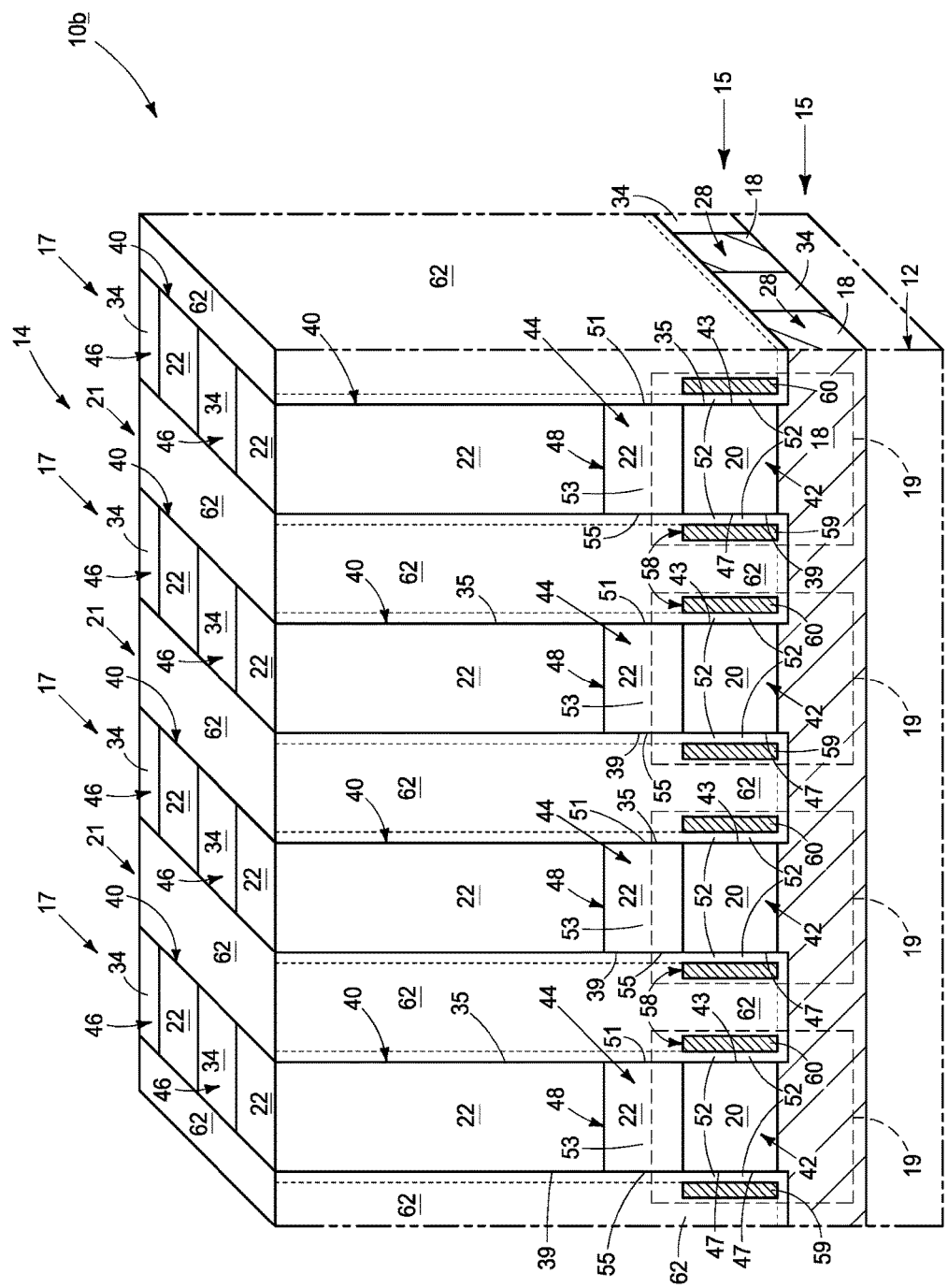
FIG. 25 is a diagrammatic perspective view of a substrate construction in process in accordance with an embodiment of the invention.

Additional example embodiments are next described with respect to a construction 10b as shown in FIGS. 25-35. Like numerals from the above-described embodiments have been used where appropriate, with some construction differences being indicated with the suffix "b" or with different numerals. FIG. 25 is analogous to FIG. 16 as described above. In FIG. 16, first material 34 and second material 62 may comprise the same or different composition materials, with FIG. 16 showing the same composition by the dashed line interfaces between first material 34 and second material 62. In FIG. 25, first material 34 and second material 62 are shown to be of different composition by a solid-line interface there-between. Regardless, in the embodiments of FIGS. 25-35 a method of forming an array of memory cells individually comprising a transistor and a capacitor comprises forming alternating first and second elevationally-extending pillars 40 and 46, respectively. First pillars 40 extend elevationally upward from digit lines 28 and individually comprise an individual channel 42 and an individual upper source/drain region 44 of individual transistors of individual memory cells within array 14. Gate insulator 52 and an access line 58 are formed laterally across a lateral side of first pillars 40 and second pillars 46 operatively laterally adjacent a lateral side of individual transistor channels 42. In one embodiment and as shown, access line 58 may be in the form of access line pairs 59, 60 that are operatively laterally adjacent a pair of first laterally-opposing sides 43, 47 of individual channels 42 of individual first pillars 40 within array 14.

Figure 26:
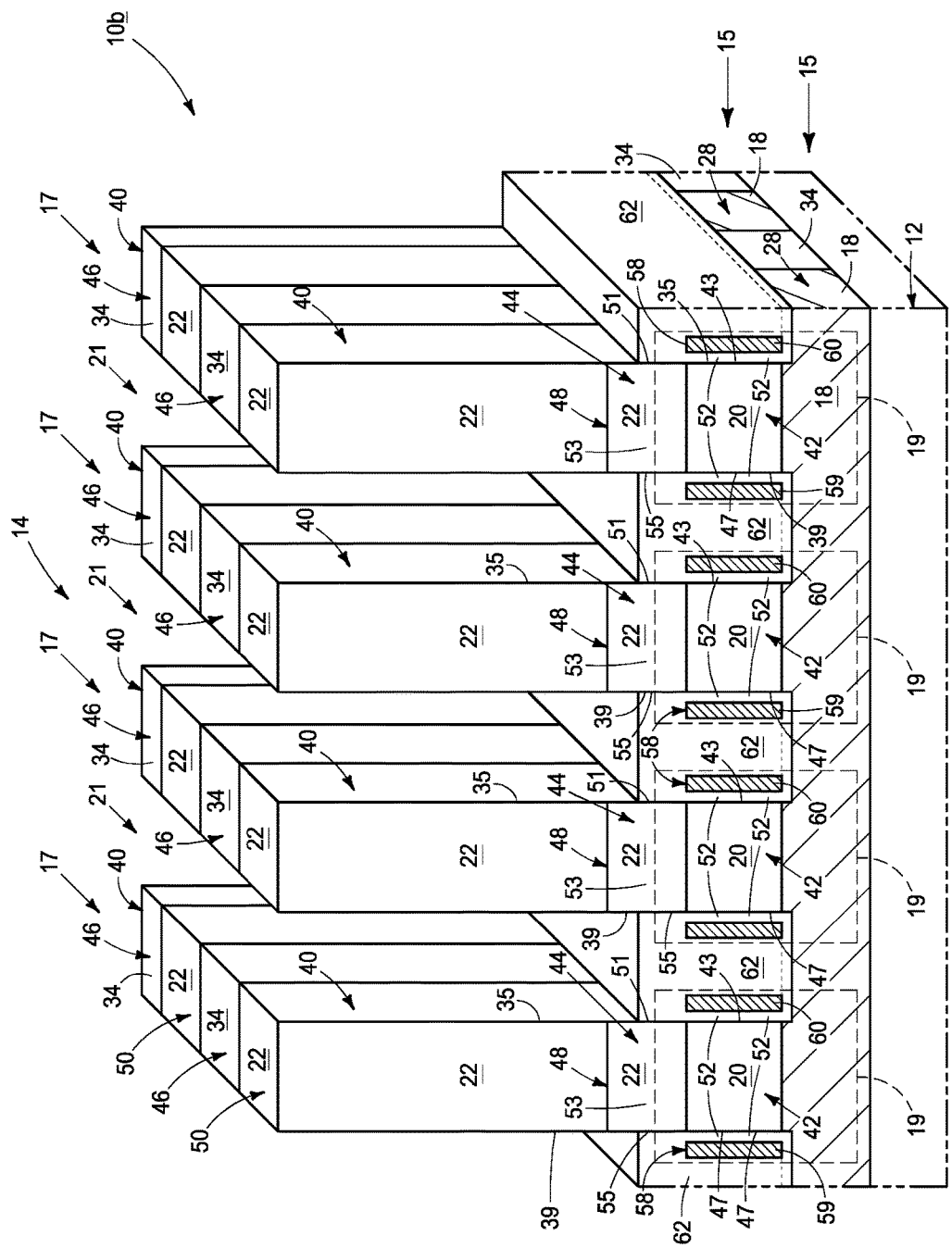
FIG. 26 is a view of the FIG. 25 construction at a processing step subsequent to that shown by FIG. 25.

Referring to FIG. 26, second material 62 has been removed back (e.g., by timed etching) selectively relative to pillar material 22 and first material 34.

Figure 27:
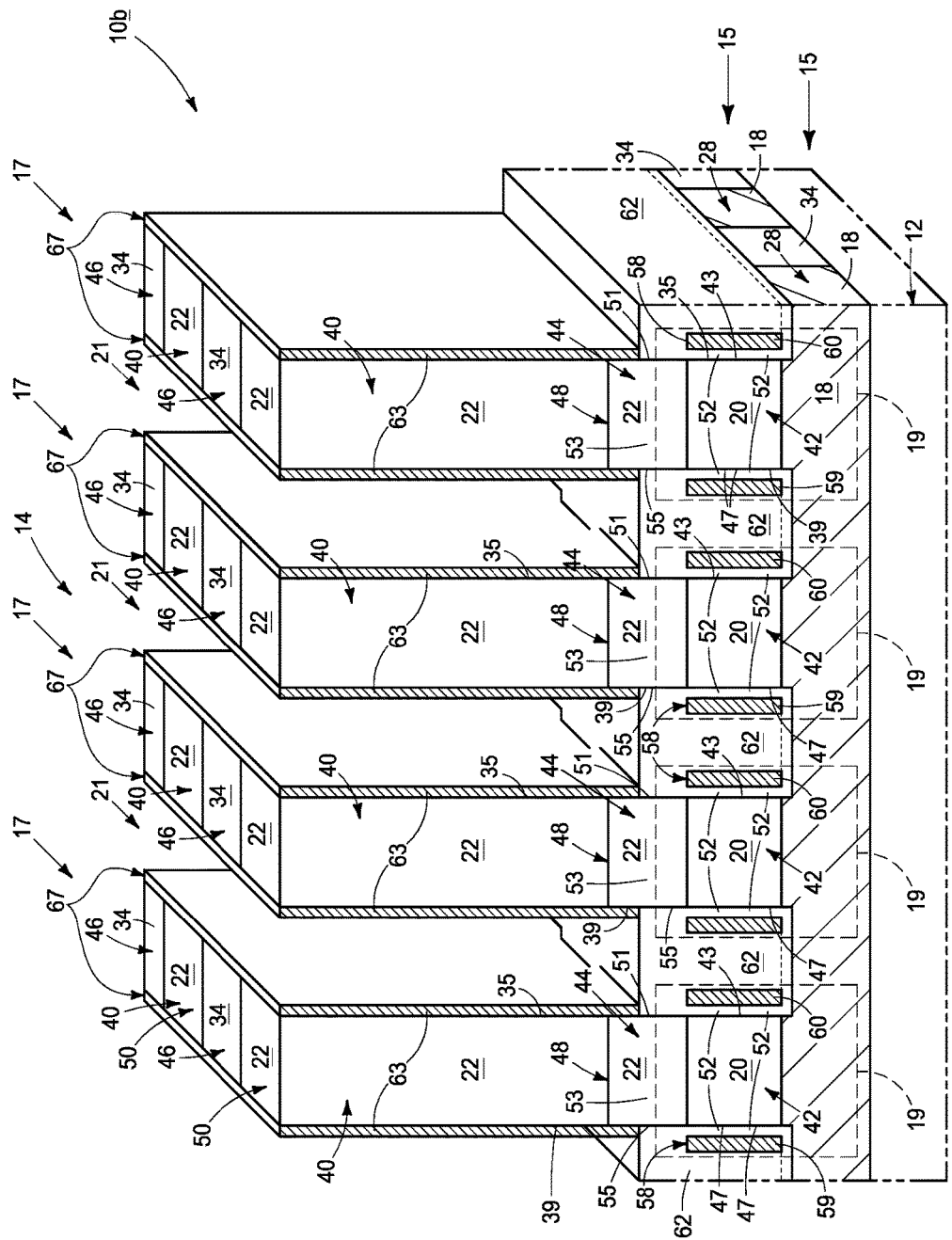
FIG. 27 is a view of the FIG. 26 construction at a processing step subsequent to that shown by FIG. 26.

Referring to FIG. 27, first capacitor electrode-comprising material 63 has been deposited and then, in one embodiment, maskless anisotropically etched (i.e., maskless at least within all of array 14) to remove such from being over pillar tops 50 and from being laterally between first pillars 40 and second pillars 46. Such is shown as forming first capacitor electrode line pairs 67 laterally across first pillars 40 and second pillars 46. First capacitor electrode line pairs 67 are directly against first laterally-opposing sides 51, 55 of individual upper source/drain regions 44 of individual first pillars 40 within array 14.

Figure 29:
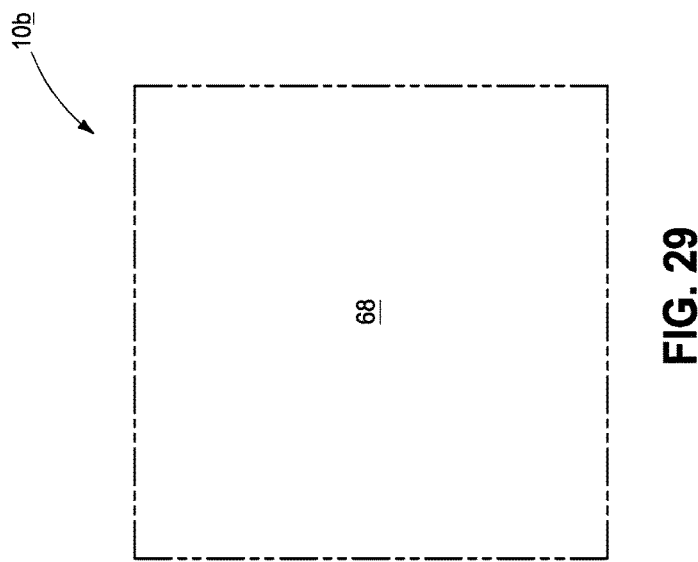
FIG. 29 is a top view through line 29-29 in FIG. 28.
Figure 28:
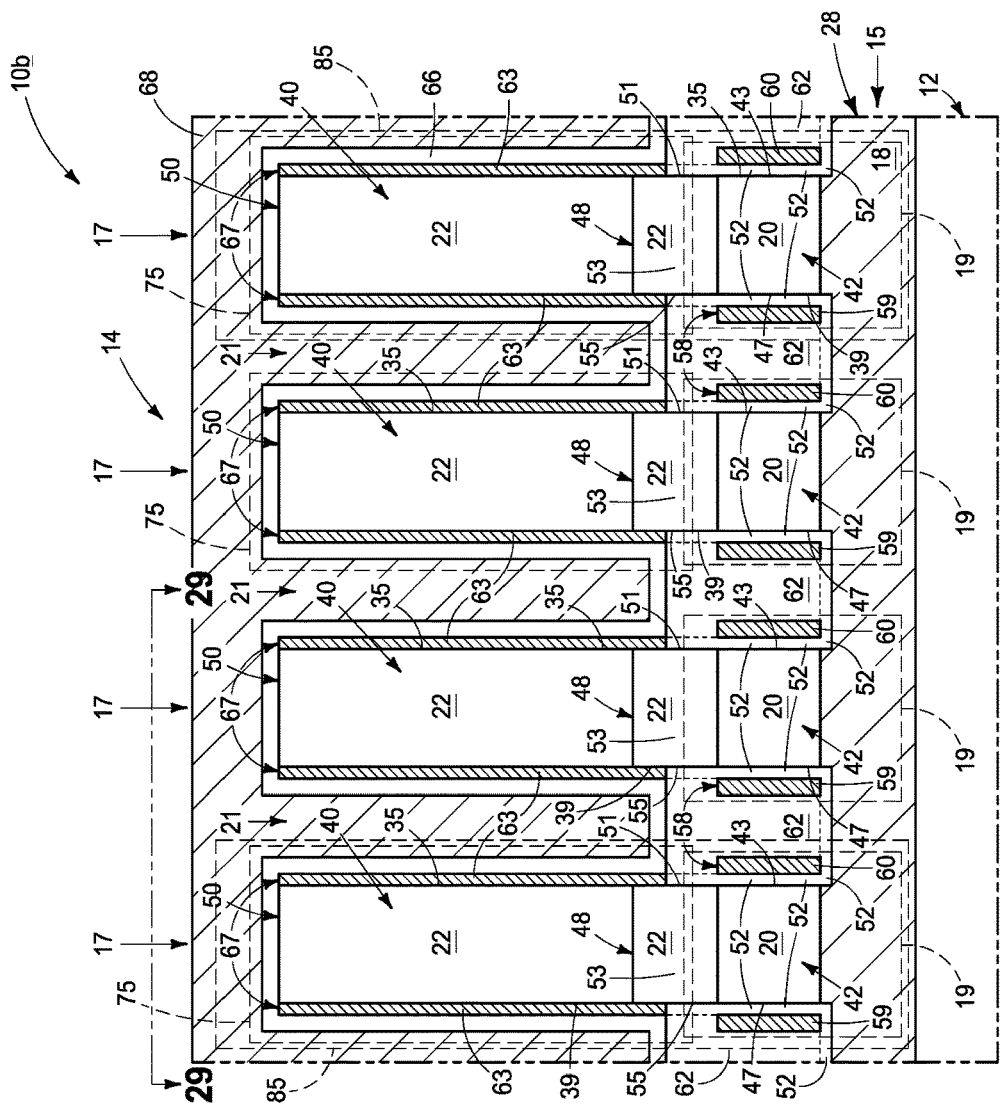
FIG. 28 is a front elevational view of the FIG. 27 construction at a processing step subsequent to that shown by FIG. 27.

Referring to FIG. 28 and FIG. 29 (a top view), capacitor insulator 66 has been formed over first capacitor electrode line pairs 67 and second capacitor electrode-comprising material 68 has been formed over capacitor insulator 66 within array 14.

Referring to FIG. 30 and FIG. 31 (a top view), materials 68 and 66 have been planarized back sufficiently to upwardly expose first material 34 (FIG. 31) of pillars 46.

Figure 32:
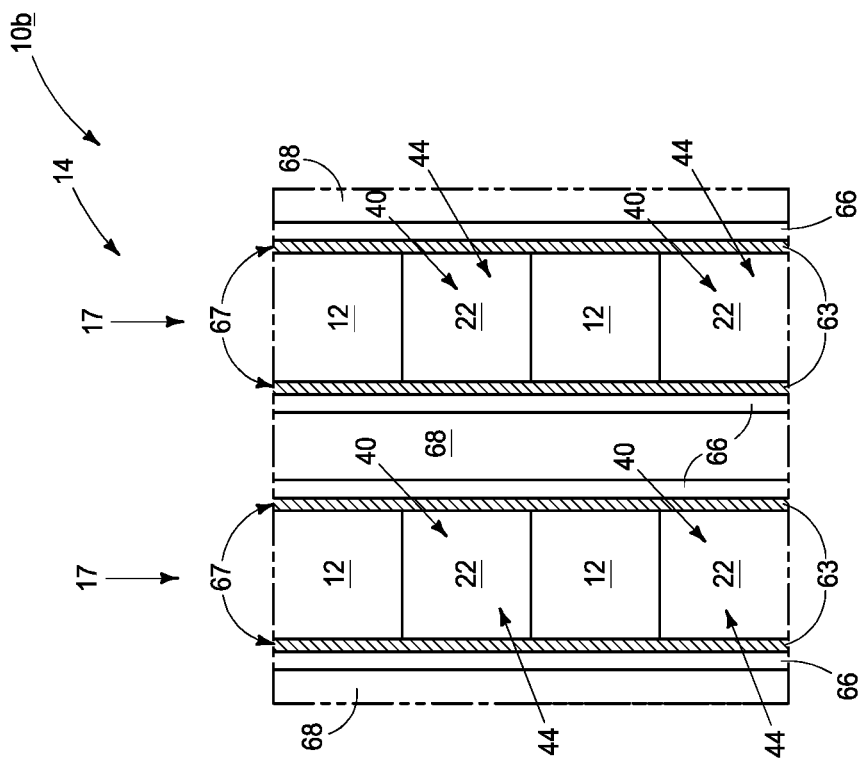
FIG. 32 is a cross-sectional view of the FIG. 31 construction at a processing step subsequent to that shown by FIG. 31 and taken horizontally through uppermost portions of upper source/drain regions 44.

Referring to FIG. 32, such is a cross-sectional view of the FIG. 31 construction at a processing step subsequent to that shown by FIG. 31 and taken horizontally through uppermost portions of upper source/drain regions 44. Material 34 (not shown) of second pillars 46 (not shown) has been removed from lateral sides of first capacitor electrode line pairs 67. In one embodiment and as shown, all material of the second pillars has been removed down to substrate 12.

Figure 33:
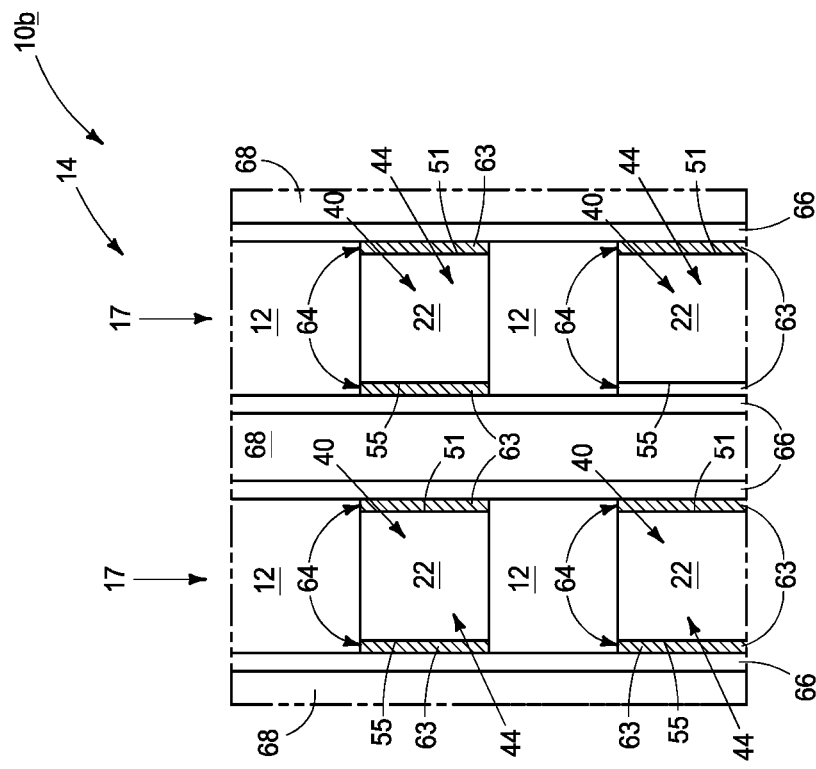
FIG. 33 is a view of the FIG. 32 construction at a processing step subsequent to that shown by FIG. 32.

Referring to FIG. 33, lateral sides of first capacitor electrode line pairs 67 (no longer shown) have been cut laterally through (e.g., by isotropic and/or anisotropic etching) to form first capacitor electrodes 64 that individually are directly against first laterally-opposing sides 51, 55 of individual upper source/drain regions 44 within array 14.

Figure 34:
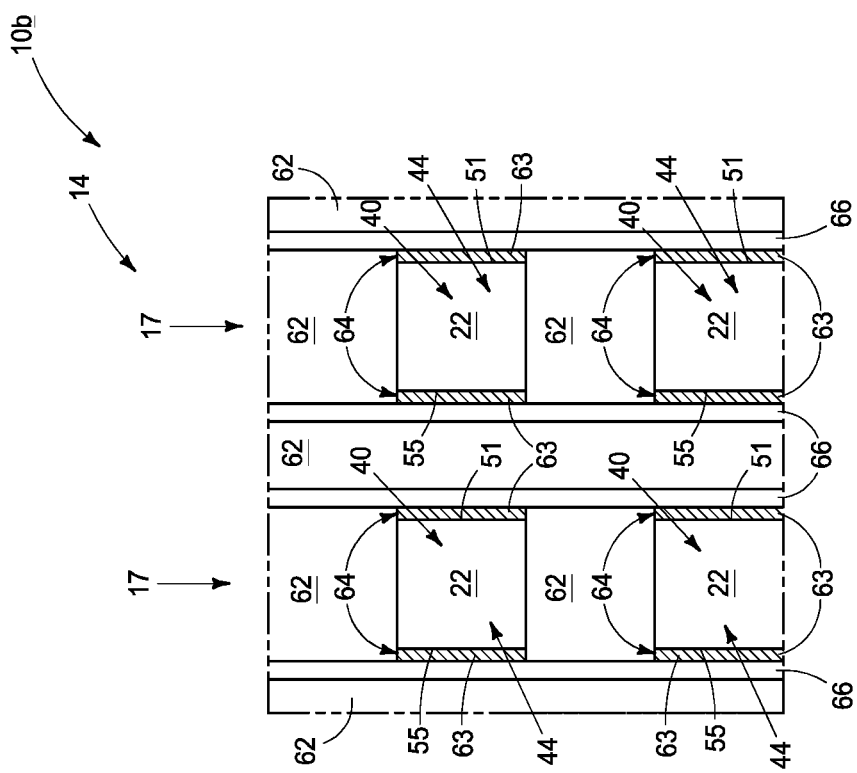
FIG. 34 is a view of the FIG. 33 construction at a processing step subsequent to that shown by FIG. 33.

Referring to FIG. 34, suitable dielectric material (e.g., material 62 as shown) has been deposited and planarized back to fill between pillars 40 (e.g., to intra-row fill within rows 17), thus effectively reforming pillars 46 (not numerically designated in FIG. 34).

Figure 35:
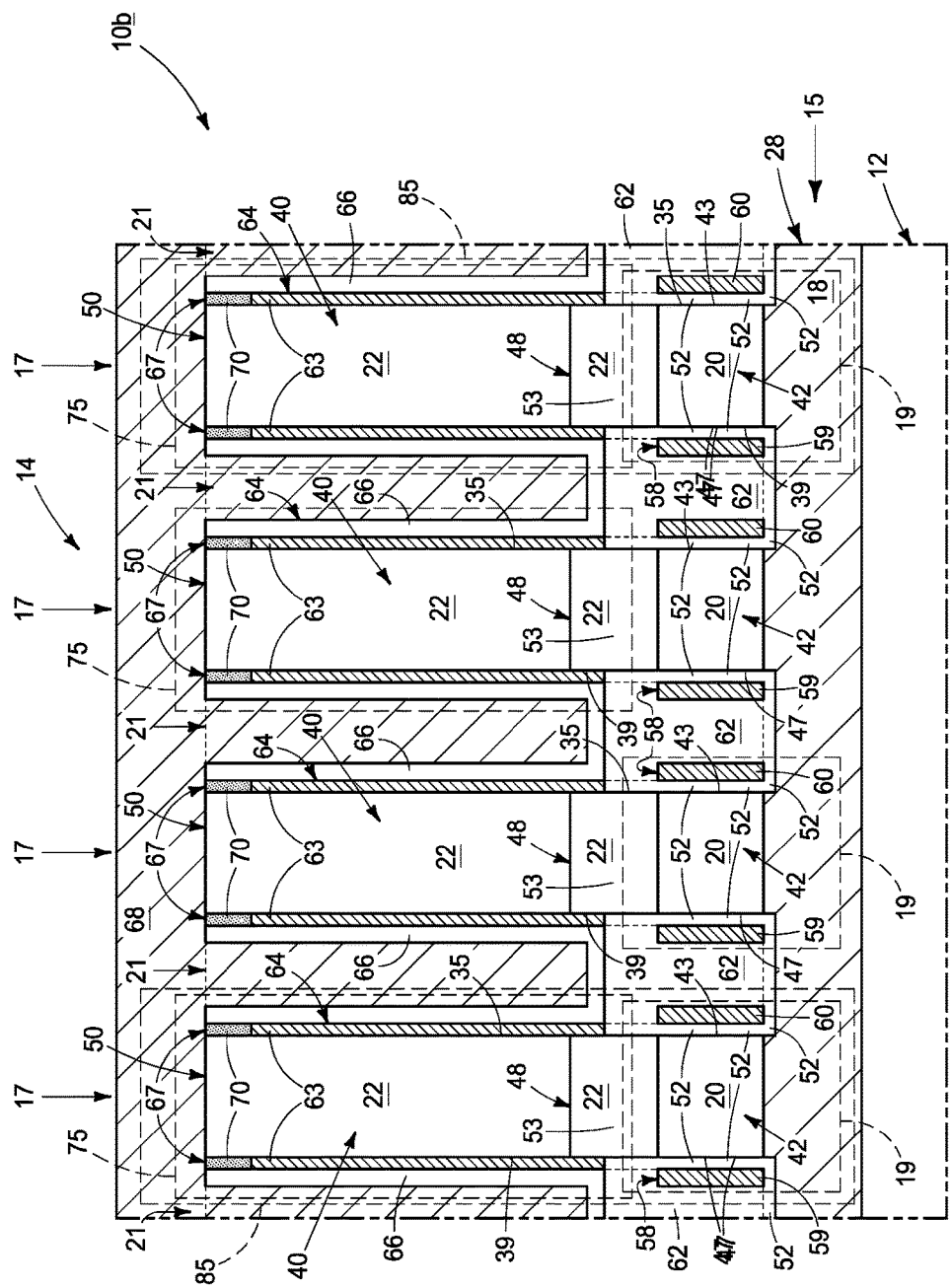
FIG. 35 is a front elevational view of the FIG. 34 construction at a processing step subsequent to that shown by FIG. 34.

Referring to FIG. 35, upper portions of first capacitor electrode-comprising material 63 have been recessed/etched back (or oxidized) and insulator material 70 (e.g., silicon dioxide or silicon nitride) has been formed there-over. Alternately, as an example, material 63 can be recessed before depositing dielectric material 62 in FIG. 34, with such dielectric material 62 then filling (not shown) such recesses. Additional second capacitor electrode-comprising material 68 has been deposited, thereby forming capacitors 75 and memory cells 85. Any other attribute(s) or aspect(s) as described herein and/or shown may be used.

The above-described embodiments with respect to FIGS. 25-35 provided the capacitor insulator over the first capacitor electrodes and the second capacitor electrode over the capacitor insulator before the stated act of laterally cutting through lateral sides of the first capacitor electrode line pairs. Alternately, the capacitor insulator and second capacitor electrode-comprising material may be provided after such act of cutting, for example as is shown and described with respect to FIGS. 36-42 with respect to a construction 10c. Like numerals from the above-described embodiments have been used where appropriate, with some construction differences being indicated with the suffix "c" or with different numerals.

Referring to FIGS. 36 and 37, construction 10c corresponds to processing of the FIG. 27 substrate to produce a different construction 10c to that shown in FIGS. 28 and 29. Specifically, in FIGS. 36 and 37, dielectric material 62 has been deposited and planarized back to fill trenches 21. Then, material 34 (not shown) of second pillars 46 (not shown) has been removed from lateral sides of first capacitor electrode line pairs 67 (e.g., instead of and before depositing capacitor materials 66 and 68).

Figure 38:
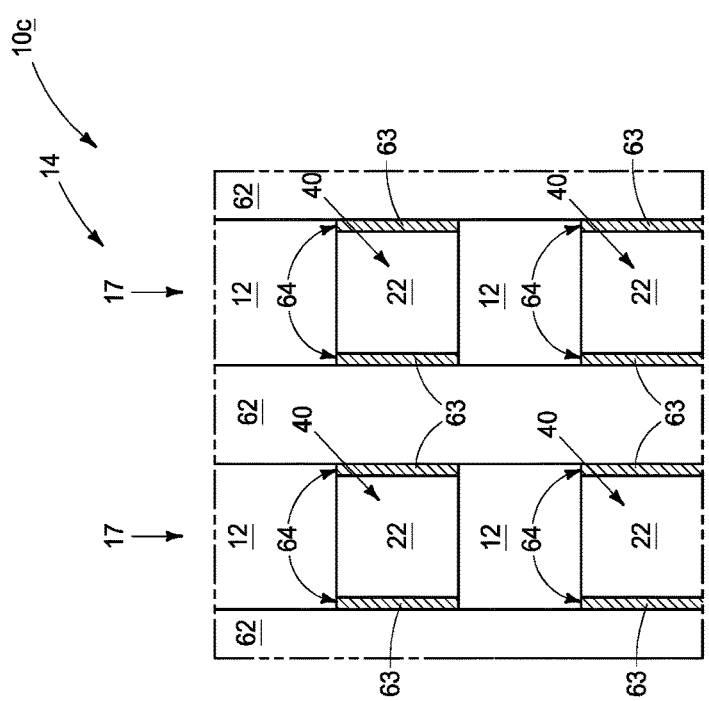
FIG. 38 is a view of the FIG. 37 construction at a processing step subsequent to that shown by FIG. 37.

Referring to FIG. 38, lateral sides of first capacitor electrode line pairs 67 (no longer shown) have been laterally cut through to form first capacitor electrodes 64.

Figure 39:
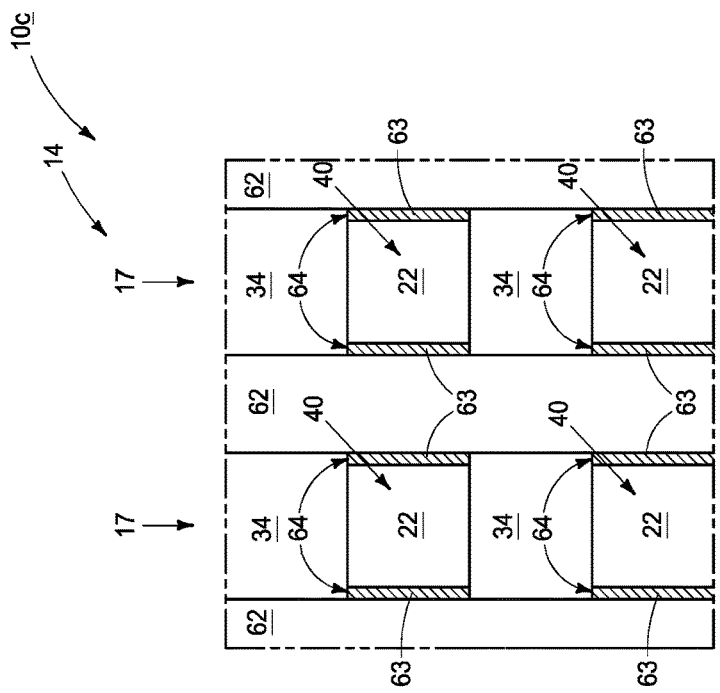
FIG. 39 is a view of the FIG. 38 construction at a processing step subsequent to that shown by FIG. 38.

Referring to FIG. 39, pillars 46 (not numerically designated in FIG. 34) have effectively been reformed by depositing and planarizing back dielectric material, for example with dielectric material 34 (e.g., silicon nitride) as shown.

Figure 40:
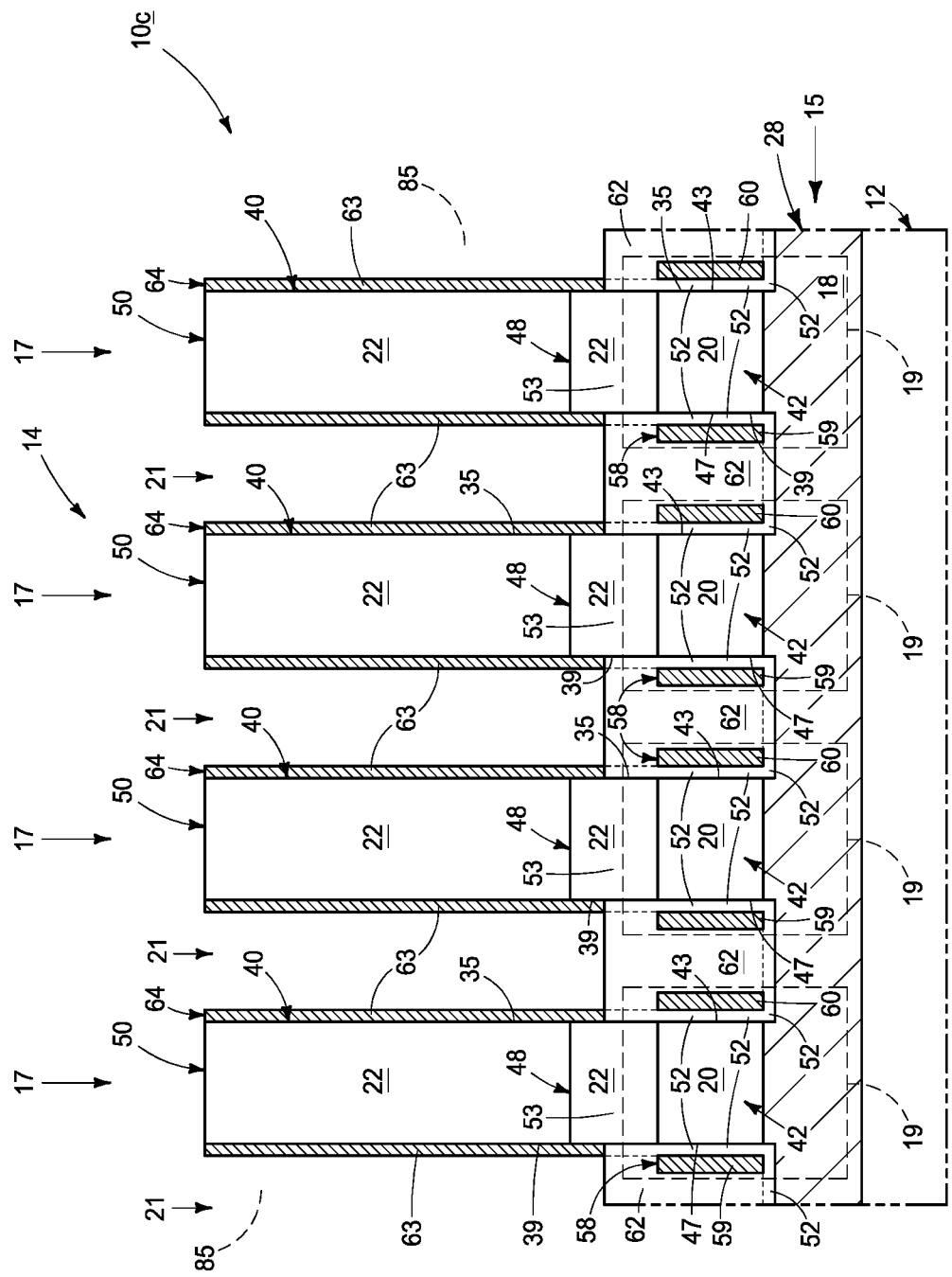
FIG. 40 is a front elevational view of the FIG. 39 construction at a processing step subsequent to that shown by FIG. 39.

Referring to FIG. 40, second material 62 has been etched back selectively relative to the other exposed materials.

Referring to FIGS. 41 and 42, capacitor insulator 66 and second capacitor electrode 68 have been subsequently formed. Any other attribute(s) or aspect(s) as described herein and/or shown may be used.

The above-described processing and figures show fabrication of, for example, one tier/deck/level of an array of memory cells. Additional such tiers/decks/levels may be provided or fabricated above or below the one tier depicted in the figures. Alternately, only a single such tier/deck/level may be fabricated.

Regardless, an embodiment of the invention encompasses a method of forming a tier of an array of memory cells within an array area, with the memory cells individually comprising a transistor and a capacitor, with the method comprising using two, and only two, sacrificial masking steps within the array area of the tier in forming the memory cells. Each of the above-described embodiments are but examples of such a method. Specifically, and for example, FIGS. 3-5 is an example one of such sacrificial masking steps (e.g., extending to FIG. 5 where at least an upper portion of material 25 is removed) and the processing shown and described above with respect to FIGS. 6 and 7 is an example another sacrificial masking step. In the above-described example embodiments and in accordance with the one embodiment of this paragraph, there are no other sacrificial masking steps within array area 14 of the depicted tier in forming the individual memory cells. Such may be facilitated by forming circuit components in a self-aligned manner. In this document, "self-aligned" means a technique whereby at least a lateral surface of a structure is defined by deposition of material against a sidewall of a previously patterned structure.

In one such embodiment, in each of the two sacrificial masking steps, exposed channel-comprising material of the transistors within the array area is subtractively etched while using sacrificial masking material above (e.g., completely covering) an unexposed portion of such channel-comprising material within the array area as a mask. In one such embodiment, in each of the two sacrificial masking steps, material is subtractively etched within the array area but none of which includes material of the capacitors within the array area. For example, neither of the masking steps shown by FIGS. 3-5 or FIGS. 6-7 etches material of the capacitors within array area 14 at least because such have not yet been formed.

In one embodiment, a sequential first of the two masking steps comprises using sacrificial masking material to mask digit line material while subtractively etching exposed digit line material away to form digit lines under the sacrificial masking material and ultimately under the transistors and capacitors formed within the array area. In one embodiment, gate material of the transistors is etched to form transistor gates and all material of which the capacitors are formed is etched to form the capacitors without any masking material being there-above within the array area during such etchings.

In one embodiment, methods in accordance with the invention comprise forming the individual memory cells to be 1T-1C. These individual memory cells are characterized by having only one transistor and only one capacitor and no other/additional operable electronic component (e.g., no other select device, etc.), yet may also include conductive material interconnecting the transistor and capacitor together and the individual memory cell to other components outside of the individual memory cells.

Embodiments of the invention also encompass forming the individual memory cells to be 2T-2C. Such memory cells are characterized by having only two transistors and only two capacitors and no other operable electronic component (e.g., no other select device, etc.), yet may also include conductive material interconnecting the two transistors to the two capacitors and the individual memory cell to other components outside of the individual memory cells. A 2T-2C memory cell architecture is shown schematically in FIG. 43 as a memory cell 2. The two transistors of the memory cell are labeled as T1 and T2, and the two capacitors are labeled as CAP-1 and CAP-2. A source/drain region of first transistor T1 connects with a node of first capacitor (CAP-1), and the other source/drain region of T1 connects with a first comparative bit line (BL-1). A gate of T1 connects with a word line (WL). A source/drain region of second transistor T2 connects with a node of second capacitor (CAP-2), and the other source/drain region of T2 connects with a second comparative bit line BL-2. A gate of T2 connects with word line WL. Each of the first and second capacitors (CAP-1 and CAP-2) has a node electrically coupled with a common plate (CP). The common plate may be coupled with any suitable voltage. Comparative bit lines BL-1 and BL-2 extend to circuitry 4 which compares electrical properties (e.g., voltage) of the two to ascertain a memory state of memory cell 2. An advantage of a 2T-2C memory cell is that a memory state may be ascertained by comparing the electrical properties of the two comparative bit lines BL-1 and BL-2 to one another. Accordingly, a reference bit line associated with other memory (for instance, 1T-1C memory) may be omitted. In such an embodiment, BL-1 and BL-2 may be electrically coupled to the same sense amplifier as part of circuitry 4.

Figure 43:
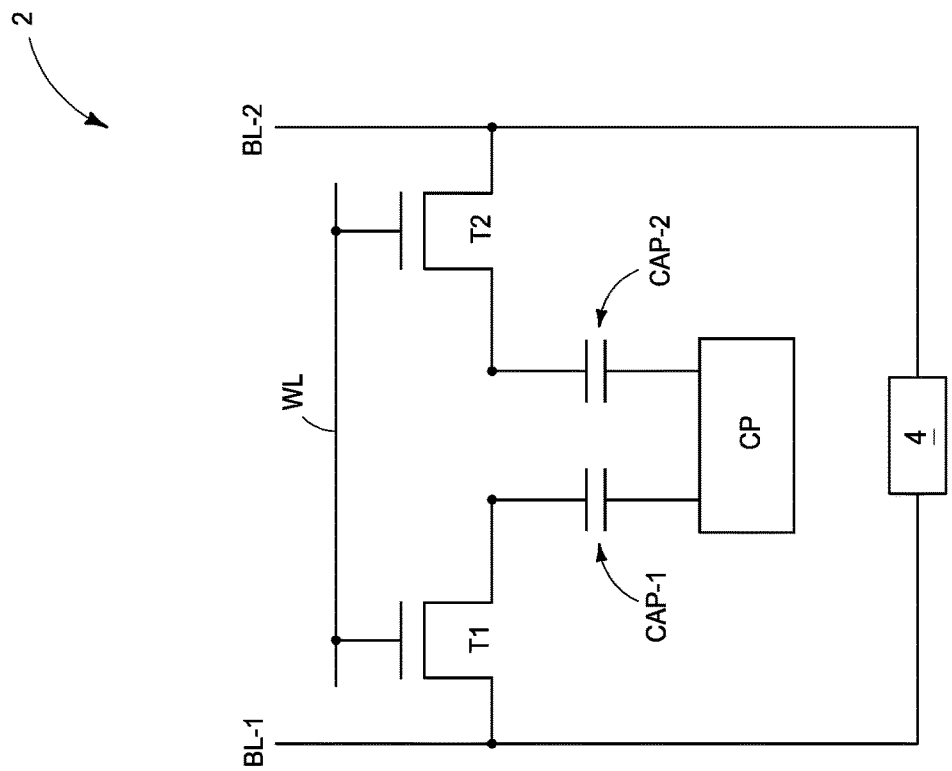
FIG. 43 is a schematic of a two transistor/two capacitor memory (2T/2C) cell in accordance with an embodiment of the invention.
Figure 44:
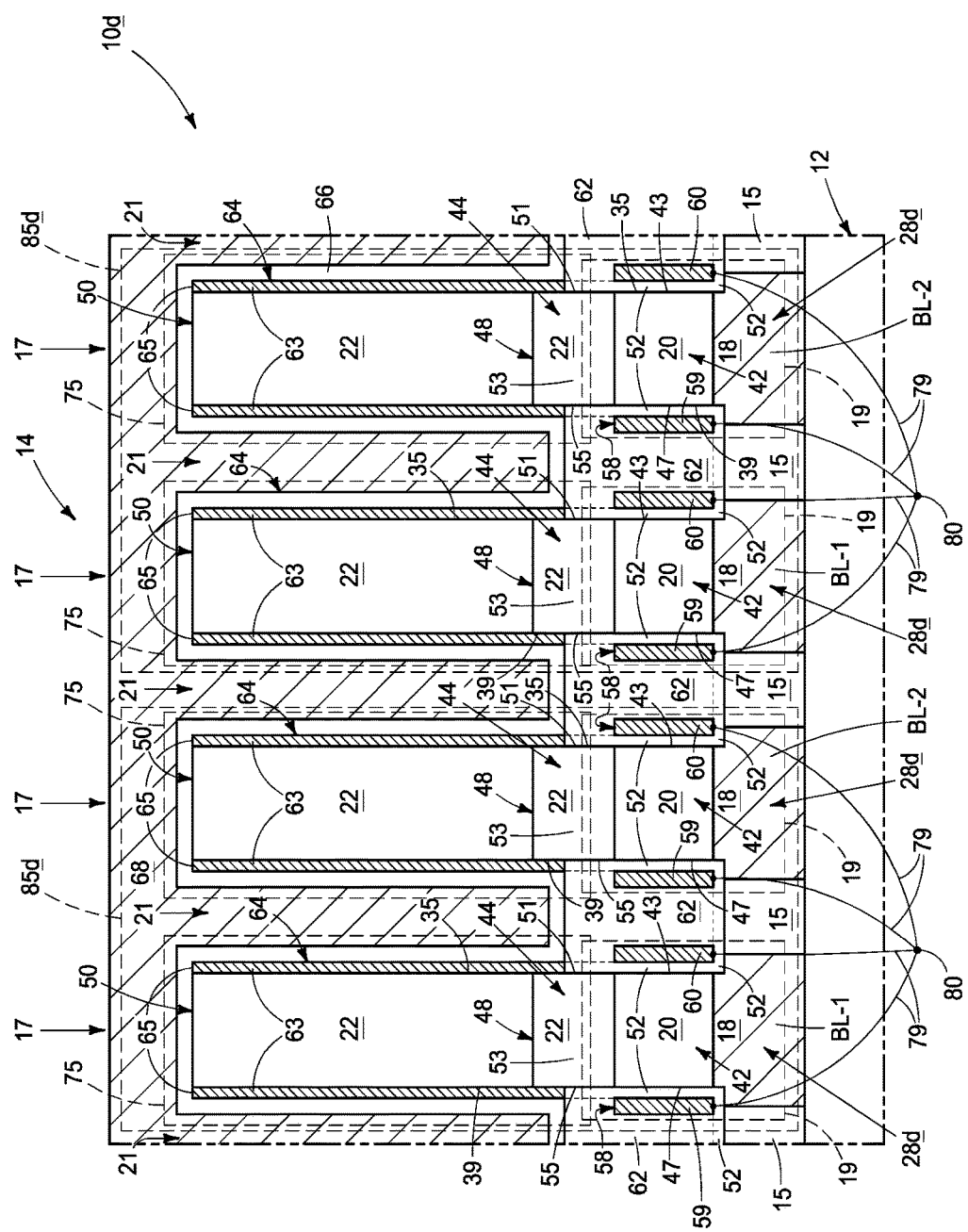
FIG. 44 is a hybrid schematic and diagrammatic front elevational view of a 2T/2C construction in accordance with an embodiment of the invention.

An alternate embodiment construction to that of FIG. 22 that may comprise 2T-2C architecture like that shown in FIG. 43 is shown in FIG. 44. Like numerals from the above-described embodiments have been used where appropriate, with some construction differences being indicated with the suffix "d". Construction 10d comprises individual memory cells 85d of 2T-2C architecture and which may be volatile or non-volatile depending on composition of the capacitor insulator. Pairs of immediately laterally adjacent transistors 19 are shown having their respective gates directly electrically coupled together to comprise one 2T-2C memory cell 85d of the array. Such is shown schematically in FIG. 44 by conductive interconnects 79 extending to a node 80 for the depicted two such individual pairs. Construction (not shown) for interconnects 79 and nodes 80 may be within and/or out-of-the-plane of the page upon which FIG. 44 lies and may be within and/or outside of array 14. Digit lines 28d (or extensions thereof) have been reconfigured as shown and in accordance with the FIG. 43 schematic for BL-1 and BL-2. Any other attribute(s) or aspect(s) as described herein and/or shown may be used.

Embodiments of the invention encompass an array (e.g., 14) of memory cells (e.g., 85, 85a, 85d) independent of the method of manufacture. However, an array of memory cells independent of method of fabrication may have any of the attribute(s) or aspect(s) as described above and/or shown. Such an array comprises rows (e.g., 17) of access lines (e.g., 58) and columns (e.g., 15) of digit lines. Individual of the columns comprise a digit line (e.g., 28) under channels (e.g., 42) of elevationally-extending transistors (e.g., 19) of individual memory cells within the array and which interconnect the transistors in that column. Individual of the rows comprise an access line above the digit lines, with the access line extending laterally across and operatively laterally adjacent a lateral side (e.g., 41, 43, 45, and/or 47) of the transistor channels and which interconnect the transistors in that row. In one embodiment, such access line comprises access line pairs (e.g., 59, 60) that extend laterally across and operatively laterally adjacent a pair of first laterally-opposing sides (e.g., 43, 47) of the transistor channels interconnecting transistors in that row.

Capacitors (e.g., 75, 75a) of the individual memory cells within the array individually comprise a first capacitor electrode (e.g., 64) directly against a lateral side (e.g., 49, 51, 53, and/or 55) of an upper source/drain region (e.g., 44) of individual of the transistors within the array. In one such embodiment, the first capacitor electrode is directly against a pair of first laterally-opposing sides (e.g., 51, 55 and/or 49, 53) of the upper source/drain region of the individual transistors within the array. In one such embodiment, the first capacitor electrode is directly against no more than two laterally-opposing sides of the upper source/drain region of the individual transistors within the array. In another such embodiment, the individual upper source/drain regions have completely encircling peripheral lateral side surfaces (e.g., 49, 51, 53, 55), with the individual first capacitor electrodes being directly against all of the completely encircling peripheral lateral side surfaces of the individual upper source/drain regions.

A capacitor insulator (e.g., 66) is over the first capacitor electrode and a second capacitor electrode (e.g., 68) is over the capacitor insulator. In one embodiment, the capacitor insulator comprises ferroelectric material.

In one embodiment, the individual memory cells comprise a pillar (e.g., 40) extending elevationally above the digit lines. The pillar comprises one of the transistor channels and an upper source/drain region of individual of the transistors. In one embodiment, such pillar has an elevational thickness that is at least three times that of the one transistor channel. In one embodiment, the pillars are formed to be conductive from the upper source/drain regions to tops (e.g., 50) of the pillars. In one embodiment, the pillars are formed to be non-conductive from tops (e.g., 48) of the upper source/drain regions to tops of the pillars. In one such embodiment, the pillars are formed to be insulative from tops of the upper source/drain regions to the pillar tops, and in another embodiment are formed to be semiconductive from tops of the upper source/drain regions to the pillar tops.

In one embodiment, the first capacitor electrode has a top (e.g., 65) that is planar and elevationally coincident with a planar top of its pillar. In another embodiment, the first capacitor electrode has a top that is not elevationally coincident with a top of its pillar. In one embodiment, the first capacitor electrode tops are planar. In one embodiment, the first capacitor electrode top is elevationally outward of its pillar top. In one embodiment, the first capacitor electrode is directly against no more than two laterally-opposing sides of the upper source/drain region of the respective individual transistors within the array. In one embodiment, the individual upper source/drain regions have completely encircling peripheral lateral side surfaces, with the individual first capacitor electrodes being directly against all of the completely encircling peripheral lateral side surfaces of the individual upper source/drain regions.

In one embodiment, capacitors of the individual memory cells within the array individually comprise an upwardly-open and downwardly-open first capacitor electrode cylinder (e.g., 64) that completely encircles and is directly against all peripheral lateral sides of an upper source/drain region of individual of the transistors within the array. In one such embodiment, the capacitor insulator and the second capacitor electrode are over a majority of the radially internal sides and a majority of the radially external sides of the first capacitor electrode cylinder. In one embodiment, the capacitor insulator is laterally over all of the radially external sides of the first capacitor electrode cylinder and laterally over only some of the radially internal sides of the first capacitor electrode cylinder. In one embodiment, the capacitor insulator is directly against tops of the encircled individual upper source/drain regions. In one embodiment, the capacitor insulator is directly against tops of the first capacitor electrode cylinders. In one embodiment, the capacitor insulator is directly against tops of the encircled individual upper source/drain regions and is directly against tops of the first capacitor electrode cylinders.

In one embodiment, the individual memory cells are 1T-1C, and in another embodiment are 2T-2C. However, the individual memory cells may be of any existing or yet-to-be developed schematic including at least one transistor and one capacitor.

Conclusion

In some embodiments, a method of forming a tier of an array of memory cells within an array area, where the memory cells individually comprise a capacitor and an elevationally-extending transistor, comprises using two, and only two, sacrificial masking steps within the array area of the tier in forming the memory cells.

In some embodiments, a method of forming an array of memory cells individually comprising a capacitor and an elevationally-extending transistor comprises using a first sacrificial mask to pattern digit line material and channel-comprising material there-above in a first direction to form digit lines within the array having lines of the channel-comprising material there-above. A second sacrificial mask is used to pattern the channel-comprising material in a second direction that is different from the first direction to cut the lines of channel-comprising material above the digit lines into spaced individual channels of individual transistors of individual memory cells within the array. Gate insulator and an access line are formed laterally across and operatively laterally adjacent a lateral side of the individual transistor channels. Capacitors are formed that individually have one of their capacitor electrodes directly against a lateral side of an upper source/drain region of one of the individual transistors of the individual memory cells within the array.

In some embodiments, a method of forming a tier of an array of memory cells individually comprising a capacitor and an elevationally-extending transistor comprises forming a digit line material over a substrate, channel-comprising material above the digit line material, and source/drain-comprising material above the channel-comprising material. The digit line material, the channel-comprising material, and the source/drain-comprising material are patterned to form digit lines within the array and to form elevationally-extending pillars comprising individual channels and individual upper source/drain regions of individual transistors of individual memory cells within the array. Gate insulator and an access line are formed laterally across and operatively laterally adjacent a lateral side of the individual transistor channels. A first capacitor electrode is formed over the first laterally-opposing sides of the pillars directly against a pair of first laterally-opposing sides of the individual upper source/drain regions within the array. Capacitor insulator is formed over the first capacitor electrode and a second capacitor electrode is formed over the capacitor insulator within the array.

In some embodiments, a method of forming an array of memory cells individually comprising a capacitor and an elevationally-extending transistor comprises forming pillars extending elevationally upward from digit lines, the pillars individually comprising an individual channel and an individual upper source/drain region of individual transistors of individual memory cells within the array. Gate insulator and an access line are formed laterally across and operatively laterally adjacent a lateral side of the individual transistor channels. A first capacitor electrode is formed that completely encircles and is directly against all peripheral lateral sides of the individual upper source/drain regions within the array. A capacitor insulator is formed over and completely encircles individual of the first capacitor electrodes and a second capacitor electrode is formed over and completely encircles the encircling capacitor insulator within the array.

In some embodiments, a method of forming an array of memory cells individually comprising a capacitor and an elevationally-extending transistor comprises forming digit line material over a substrate, channel-comprising material above the digit line material, and source/drain-comprising material above the channel-comprising material. The digit line material, the channel-comprising material, and the source/drain-comprising material are patterned in a first direction to form digit lines within the array having lines of the channel-comprising material and lines of the source/drain-comprising material there-above. First material is formed in trenches that are laterally between the digit lines and the lines there-above within the array. The channel-comprising material, the source/drain-comprising material, and the first material are patterned in a second direction that is different from the first direction to form elevationally-extending pillars comprising individual channels and individual upper source/drain regions of individual transistors of individual memory cells within the array and having the first material laterally between the pillars. Gate insulator and access line pairs are formed laterally across a pair of first laterally-opposing sides of the pillars operatively laterally adjacent a pair of first laterally-opposing sides of the individual channels within the array. Second material is formed in trenches that are laterally between the pillars and the first material within the array. The first and second materials are removed sufficiently to expose encircling peripheral lateral sides of the individual upper source/drain regions. A first capacitor electrode is formed that completely encircles and is directly against all of the encircling peripheral lateral sides of the individual upper source/drain regions within the array. A capacitor insulator is formed over and completely encircles individual of the first capacitor electrodes and a second capacitor electrode is formed over and completely encircles the encircling capacitor insulator within the array.

In some embodiments, a method of forming an array of memory cells individually comprises a capacitor and an elevationally-extending transistor comprises forming alternating first and second elevationally-extending pillars, the first pillars extending elevationally upward from digit lines and individually comprising an individual channel and an individual upper source/drain region of individual transistors of individual memory cells within the array. Gate insulator and an access line are formed laterally across and operatively laterally adjacent a lateral side of the individual transistor channels. First capacitor electrode line pairs are formed laterally across the first and second pillars. The first capacitor electrode line pairs are directly against a pair of first laterally-opposing sides of the individual upper source/drain regions of the individual first pillars within the array. Material of the second pillars if removed from lateral sides of the first capacitor electrode line pairs and then cutting is conducted laterally through the lateral sides of the first capacitor electrode line pairs to form first capacitor electrodes that individually are directly against the first laterally-opposing sides of the individual upper source/drain regions within the array. A capacitor insulator is provided over the first capacitor electrodes and a second capacitor electrode is provided over the capacitor insulator within the array.

In some embodiments, an array of memory cells individually comprising a capacitor and an elevationally-extending transistor, and where the array comprises rows of access lines and columns of digit lines, has individual of the columns comprising a digit line under channels of elevationally-extending transistors of individual memory cells within the array and interconnects the transistors in that column. Individual of the rows comprise an access line above the digit lines. The access line extends laterally across and operatively laterally adjacent a lateral side of the transistor channels and interconnect the transistors in that row.

Capacitors of the individual memory cells within the array individually comprise a first capacitor electrode directly against a lateral side of an upper source/drain region of individual of the transistors within the array. A capacitor insulator is over the first capacitor electrode. A second capacitor electrode is over the capacitor insulator.

In some embodiments, an array of memory cells individually comprising a capacitor and an elevationally-extending transistor, and where the array comprises rows of access lines and columns of digit lines, has individual of the columns comprising a digit line under channels of elevationally-extending transistors of individual memory cells within the array and interconnects the transistors in that column. Individual of the rows comprise an access line above the digit lines. The access line extends laterally across and operatively laterally adjacent a lateral side of the transistor channels and interconnects the transistors in that row. Capacitors of the individual memory cells within the array individually comprise a first capacitor electrode directly against a pair of first laterally-opposing sides of an upper source/drain region of individual of the transistors within the array. A capacitor insulator is over the first capacitor electrode. A second capacitor electrode is over the capacitor insulator.

In some embodiments, an array of memory cells individually comprising a capacitor and an elevationally-extending transistor, and where the array comprises rows of access lines and columns of digit lines, has individual of the columns comprising a digit line under channels of elevationally-extending transistors of individual memory cells within the array and interconnects the transistors in that column. Individual of the rows comprise an access line above the digit lines. The access line extends laterally across and operatively laterally adjacent a lateral side of the transistor channels and interconnects the transistors in that row. The individual memory cells comprise a pillar extending elevationally above the digit lines. The pillar comprises one of the transistor channels and an upper source/drain region of individual of the transistors. The pillar having an elevational thickness that is at least three times that of the one transistor channel. Capacitors of the individual memory cells within the array individually comprise a first capacitor electrode directly against a pair of first laterally-opposing sides of the pillar and the upper source/drain region of the respective one individual transistor within the array. A capacitor insulator is over the first capacitor electrode. A second capacitor electrode is over the capacitor insulator.

In some embodiments, an array of memory cells individually comprising a capacitor and an elevationally-extending transistor, and where the array comprises rows of access lines and columns of digit lines, has individual of the columns comprising a digit line under channels of elevationally-extending transistors of individual memory cells within the array and interconnects the transistors in that column. Individual of the rows comprise an access line above the digit lines. The access line extends laterally across and operatively laterally adjacent a lateral side of the transistor channels and interconnects the transistors in that row. Capacitors of the individual memory cells within the array individually comprise an upwardly-open and downwardly-open first capacitor electrode cylinder completely encircling and directly against all peripheral lateral sides of an upper source/drain region of individual of the transistors within the array. A capacitor insulator is over radially outer sides and radially inner sides of the first capacitor electrode cylinder. A second capacitor electrode is over the capacitor insulator and over the radially outer sides and the radially inner sides of the first capacitor electrode cylinder.

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

The invention claimed is:

1. A tier of memory cells comprising:
   a first memory cell and a second memory cell laterally adjacent the first memory cell;
   the first memory cell comprising:
      a first capacitor and a first vertical transistor;
      the first vertical transistor comprising a first pillar comprising a channel and an upper source/drain region above the channel of the first vertical transistor, the channel of the first vertical transistor being above and electrically coupled to a digit line; and
      the first capacitor comprising a first bottom electrode directly against a lateral side of the upper source/drain region of the first vertical transistor;
   the second memory cell comprising:
      a second capacitor and a second vertical transistor;
      the second vertical transistor comprising a second pillar comprising a channel and an upper source/drain region above the channel of the second vertical transistor, the channel of the second vertical transistor being above and electrically coupled to the digit line; and
      the second capacitor comprising a second bottom electrode directly against a lateral side of the upper source drain region of the second vertical transistor; and
   the first capacitor and the second capacitor sharing a common top electrode.

2. The tier of memory cells of claim 1 wherein at least a portion of a gate of the first vertical transistor and at least a portion of a gate of the second vertical transistor are laterally between the channel of the first vertical transistor and the channel of the second vertical transistor, the gate of the first vertical transistor being separated from the gate of the second vertical transistor by an insulative material.

3. The tier of memory cells of claim 1 wherein each of the first bottom electrode and the second bottom electrode is a cylinder.

4. The tier of memory cells of claim 3 wherein each of the cylinders is an upwardly open cylinder.

5. The tier of memory cells of claim 3 wherein each of the cylinders is a downwardly open cylinder.

6. The tier of memory cells of claim 3 wherein each of the cylinders is an upwardly open and downwardly open cylinder.

7. The tier of memory cells of claim 1 wherein,
   the channel of the first vertical transistor has a vertical sidewall that is aligned with a vertical sidewall of the upper source/drain region of the first transistor; and
   the channel of the second vertical transistor has a vertical sidewall that is aligned with a vertical sidewall of the upper source/drain region of the second transistor.

8. The tier of memory cells of claim 1 wherein,
   the channel of the first vertical transistor has a vertical sidewall that is aligned with a vertical sidewall of the first bottom electrode; and the channel of the second vertical transistor has a vertical sidewall that is aligned with a vertical sidewall of the second bottom electrode.

9. The tier of memory cells of claim 8 wherein,
the vertical sidewall of the channel of the first vertical transistor is aligned with a vertical sidewall of the upper source/drain region of the first transistor; and
the vertical sidewall of the channel of the second vertical transistor is aligned with a vertical sidewall of the upper source/drain region of the second transistor.

10. The tier of memory cells of claim 1 wherein the first and the second bottom electrodes comprise TiN.

11. The tier of memory cells of claim 1 wherein,
each of the channel of the first vertical transistor and the channel of the second vertical transistor has a pair of laterally opposing sides;
each of the first vertical transistor and the second vertical transistor comprises a gate;
the gate of the first vertical transistor being laterally over each of the pair of laterally opposing sides of the channel of the first vertical transistor; and
the gate of the second vertical transistor being laterally over each of the pair of laterally opposing sides of the channel of the second vertical transistor.

12. The tier of memory cells of claim 11 wherein,
the gate of the first vertical transistor does not radially surround the channel of the first vertical transistor; and
the gate of the second vertical transistor does not radially surround the channel of the second vertical transistor.

13. The tier of memory cells of claim 1 wherein each of the first vertical transistor and the second vertical transistor comprises a gate comprising TiN.

14. The tier of memory cells of claim 1 comprising a capacitor insulator between the first bottom electrode and the common top electrode and between the second bottom electrode and the common top electrode, the capacitor insulator being across tops of the first and second pillars, the common top electrode being across the tops of the first and second pillars above the capacitor insulator that is across the tops of the first and second pillars.

15. The tier of memory cells of claim 1 wherein each of the first bottom electrode and the second bottom electrode is a cylinder, and further comprising:
a capacitor insulator between the first bottom electrode and the common top electrode and between the second bottom electrode and the common top electrode; and
the capacitor insulator and the common top electrode being on internal and external sides of the cylinder of each of the first and second bottom electrodes.

16. The tier of memory cells of claim 1 wherein each of the first vertical transistor and the second vertical transistor comprises a gate, the upper source/drain region of each of the first and second vertical transistors having a top that is higher than a top of each of the gates.

17. The tier of memory cells of claim 1 wherein,
the first bottom electrode surrounds and is directly against all uppermost lateral sides of the upper source/drain region of the first vertical transistor; and
the second bottom electrode surrounds and is directly against all uppermost lateral sides of the upper source/drain region of the second vertical transistor.

18. The tier of memory cells of claim 1 wherein each of the upper source/drain region of each of the first and second vertical transistors has a top, the common top electrode comprising at least a portion thereof that is lower than the top of each of the first and second vertical transistors.

19. The tier of memory cells of claim 1 wherein the first and second memory cells each have a total of only one transistor and a total of only one capacitor.

20. The tier of memory cells of claim 1 wherein the first and second memory cells each have a total of only two transistors and a total of only one capacitor.

21. Multiple stacked tiers of memory cells, individual of the tiers of memory cells comprising:
a first memory cell and a second memory cell laterally adjacent the first memory cell;
the first memory cell comprising:
a first capacitor and a first vertical transistor;
the first vertical transistor comprising a first pillar comprising a channel and an upper source/drain region above the channel of the first vertical transistor, the channel of the first vertical transistor being above and electrically coupled to a digit line; and
the first capacitor comprising a first bottom electrode directly against a lateral side of the upper source/drain region of the first vertical transistor;
the second memory cell comprising:
a second capacitor and a second vertical transistor;
the second vertical transistor comprising a second pillar comprising a channel and an upper source/drain region above the channel of the second vertical transistor, the channel of the second vertical transistor being above and electrically coupled to the digit line; and
the second capacitor comprising a second bottom electrode directly against a lateral side of the upper source drain region of the second vertical transistor;
the first capacitor and the second capacitor sharing a common top electrode; and
the first and second memory cells each have a total of only one transistor and a total of only one capacitor.

22. Multiple stacked tiers of memory cells, individual of the tiers of memory cells comprising:
a first memory cell and a second memory cell laterally adjacent the first memory cell;
the first memory cell comprising:
a first capacitor and a first vertical transistor;
the first vertical transistor comprising a first pillar comprising a channel and an upper source/drain region above the channel of the first vertical transistor, the channel of the first vertical transistor being above and electrically coupled to a digit line; and
the first capacitor comprising a first bottom electrode directly against a lateral side of the upper source/drain region of the first vertical transistor;
the second memory cell comprising:
a second capacitor and a second vertical transistor;
the second vertical transistor comprising a second pillar comprising a channel and an upper source/drain region above the channel of the second vertical transistor, the channel of the second vertical transistor being above and electrically coupled to the digit line; and
the second capacitor comprising a second bottom electrode directly against a lateral side of the upper source drain region of the second vertical transistor; and
the first capacitor and the second capacitor sharing a common top electrode.

23. The tier of memory cells of claim 22 wherein the first and second memory cells each have a total of only two transistors and a total of only one capacitor.

* * * * *